United States Patent
Lynch

(10) Patent No.: US 12,036,041 B2
(45) Date of Patent: Jul. 16, 2024

(54) WEARABLE ASSEMBLY COMPRISING A WEARABLE ARTICLE AND AN ELECTRONICS MODULE

(71) Applicant: Prevayl Innovations Limited, Manchester (GB)

(72) Inventor: Michael John Lynch, Cheshire (GB)

(73) Assignee: Prevayl Innovations Limited, Manchester (GB)

( * ) Notice: Subject to any disclaimer, the term of this patent is extended or adjusted under 35 U.S.C. 154(b) by 101 days.

(21) Appl. No.: 17/857,121

(22) Filed: Jul. 4, 2022

(65) Prior Publication Data

US 2023/0010015 A1 Jan. 12, 2023

Related U.S. Application Data

(63) Continuation of application No. 17/790,750, filed as application No. PCT/GB2021/050395 on Feb. 18, 2021.

(30) Foreign Application Priority Data

Feb. 19, 2020 (GB) ..................... 2002254

(51) Int. Cl.
*A61B 5/00* (2006.01)
*A41C 3/00* (2006.01)
*A41D 1/00* (2018.01)

(52) U.S. Cl.
CPC .......... *A61B 5/6804* (2013.01); *A41C 3/0064* (2013.01); *A41D 1/002* (2013.01);
(Continued)

(58) Field of Classification Search
CPC ........ A61B 2503/10; A61B 2560/0219; A61B 2560/0242; A61B 2560/045; A61B 5/021;
(Continued)

(56) References Cited

U.S. PATENT DOCUMENTS

| | | | |
|---|---|---|---|
| 9,242,093 B1 | 1/2016 | Sherman | |
| 10,156,029 B1 | 12/2018 | Podhajny | |

(Continued)

FOREIGN PATENT DOCUMENTS

| | | |
|---|---|---|
| CN | 104739369 | 7/2015 |
| EP | 2505090 | 10/2012 |

(Continued)

OTHER PUBLICATIONS

Examination Report received in GB2002253.9 mailed Aug. 23, 2022.

(Continued)

*Primary Examiner* — Shahdeep Mohammed
(74) *Attorney, Agent, or Firm* — Suzannah K. Sundby, Esq.; Canady + Lortz LLP

(57) ABSTRACT

The wearable article 200 comprises a sensing component. The electronics module 100 is removably coupled to the wearable article 200. The electronics module comprises a housing and a processor disposed within the housing 101. An interface element 121, 123 interfaces with the sensing component so as to receive signals from the sensing component and provide the same to the processor. A sensor 105 is disposed within the housing 101. The sensor 105 monitors a property of the environment external to the electronics module 100 through the housing 101. The housing 101 is constructed such that the sensor 105 has line of sight through the housing 101.

19 Claims, 12 Drawing Sheets

(52) U.S. Cl.
CPC ............ *A61B 5/002* (2013.01); *A61B 5/0059* (2013.01); *A61B 2503/10* (2013.01); *A61B 2560/0214* (2013.01); *A61B 2562/166* (2013.01)

(58) Field of Classification Search
CPC ............ A61B 5/02405; A61B 5/02416; A61B 5/0537; A61B 5/073; A61B 5/1112; A61B 5/1118; A61B 5/112; A61B 5/318; A61B 5/6824; A61B 5/7455; A61B 2560/0412; A61B 2562/0219; A61B 5/0004; A61B 5/02427; A61B 5/02438; A61B 5/0816; A61B 5/1116; A61B 5/113; A61B 5/14551; A61B 5/6801; A61B 5/6802; A61B 5/6804; A61B 5/6823; A61B 5/721
See application file for complete search history.

(56) References Cited

U.S. PATENT DOCUMENTS

| | | | |
|---|---|---|---|
| 10,537,284 | B1 | 1/2020 | Ruh |
| 2002/0124295 | A1* | 9/2002 | Fenwick ............ A41D 13/1245 2/69 |
| 2002/0165436 | A1 | 11/2002 | Schluter |
| 2007/0299325 | A1 | 12/2007 | Farrell |
| 2008/0184459 | A1 | 8/2008 | Barnes |
| 2010/0324972 | A1 | 12/2010 | Brooke |
| 2013/0321168 | A1* | 12/2013 | Mahony ................. A61B 5/318 340/870.07 |
| 2014/0081368 | A1 | 3/2014 | Szeles |
| 2014/0249613 | A1* | 9/2014 | Kaib .................... A61N 1/0496 607/152 |
| 2014/0361147 | A1 | 12/2014 | Fei |
| 2015/0128327 | A1 | 5/2015 | Martinez |
| 2015/0145742 | A1 | 5/2015 | Cao |
| 2015/0173675 | A1 | 6/2015 | Shimizu |
| 2015/0297137 | A1* | 10/2015 | Welch ................. A61B 5/14535 600/344 |
| 2016/0036118 | A1 | 2/2016 | Baringer |
| 2016/0061726 | A1 | 3/2016 | Ness |
| 2016/0135516 | A1 | 5/2016 | Cobbett |
| 2016/0171646 | A1 | 6/2016 | Breedvelt-Schouten |
| 2016/0192716 | A1 | 7/2016 | Lee |
| 2016/0211877 | A1 | 7/2016 | Poon |
| 2016/0282187 | A1 | 9/2016 | Sun |
| 2016/0324432 | A1 | 11/2016 | Ahmed |
| 2016/0374567 | A1 | 12/2016 | Breslow |
| 2017/0000415 | A1 | 1/2017 | Lapetina |
| 2017/0014035 | A1 | 1/2017 | Newberry |
| 2017/0071545 | A1 | 3/2017 | Ritscher |
| 2017/0106183 | A1 | 4/2017 | Silver |
| 2017/0143977 | A1 | 5/2017 | Kaib |
| 2017/0224236 | A1 | 8/2017 | Ho |
| 2017/0258329 | A1 | 9/2017 | Marsh |
| 2017/0315511 | A1 | 11/2017 | Shim |
| 2017/0319132 | A1 | 11/2017 | Longinotti-Buitoni |
| 2017/0325698 | A1 | 11/2017 | Allec |
| 2017/0354348 | A1* | 12/2017 | Winter .................... G06F 30/20 |
| 2018/0008150 | A1 | 1/2018 | Hsieh |
| 2018/0070839 | A1 | 3/2018 | Ritscher |
| 2018/0085283 | A1 | 3/2018 | Rahman |
| 2018/0144113 | A1 | 5/2018 | Cho |
| 2018/0220962 | A1* | 8/2018 | Palley .................. A61B 5/0004 |
| 2018/0295896 | A1 | 10/2018 | Donohoe |
| 2018/0303381 | A1 | 10/2018 | Todd |
| 2019/0046033 | A1* | 2/2019 | Gannon ................. G01K 1/024 |
| 2019/0099116 | A1 | 4/2019 | Wiese |
| 2019/0110748 | A1 | 4/2019 | Cho |
| 2019/0110755 | A1 | 4/2019 | Capodilupo |
| 2019/0132948 | A1* | 5/2019 | Longinotti-Buitoni ...... A61B 5/743 |
| 2019/0159680 | A1 | 5/2019 | Tanaka |
| 2019/0196411 | A1 | 6/2019 | Yuen |
| 2019/0227022 | A1* | 7/2019 | Harley-Trochimczyk ................. A61B 5/7203 |
| 2019/0261888 | A1 | 8/2019 | Zdeblick |
| 2021/0007617 | A1 | 1/2021 | Kim |

FOREIGN PATENT DOCUMENTS

| | | |
|---|---|---|
| EP | 3332698 | 6/2018 |
| GB | 2516214 | 1/2015 |
| GB | 2590986 | 7/2021 |
| GB | 2590988 | 7/2021 |
| GB | 2591819 | 8/2021 |
| GB | 2591820 | 8/2021 |
| GB | 2591821 | 8/2021 |
| GB | 2592362 | 9/2021 |
| GB | 2593433 | 9/2021 |
| GB | 2593434 | 9/2021 |
| GB | 2596440 | 12/2021 |
| GB | 2590985 | 4/2022 |
| JP | 11128183 | 5/1999 |
| WO | 2004110192 | 12/2004 |
| WO | 2015134654 | 9/2015 |
| WO | 2018025199 | 2/2018 |
| WO | 2019168475 | 9/2019 |
| WO | 2019197878 | 10/2019 |
| WO | 2019198991 | 10/2019 |
| WO | 2019213054 | 11/2019 |
| WO | 2019213079 | 11/2019 |
| WO | 2019213114 | 11/2019 |

OTHER PUBLICATIONS

Prosecution history of GB2590988.
Prosecution history of GB2596440.
International Search Report received in PCT/GB2021/050395 mailed May 28, 2021.
Written Opinion received in PCT/GB2021/050395 mailed May 28, 2021.
https://twitter.com/whoop/status/1058009907386085381, Publisher: Twitter posts dated Oct. 30, 2018 and Nov. 1, 2018.
https://www.prnewswire.com/news-releases/introducing-whoop-strap-3-0-featuring-whoop-live-300855111.html, Introducing Whoop Strap 3.0 Featuring Whoop Live, May 22, 2019, Publisher: Whoop.
Search and Examination Report received in GB2205756.6 mailed Sep. 30, 2022.
https://www.whoop.com/en-gb/thelocker/whoop-4-0-vs-3-0-whats-new/, Whoop 4.0 vs. 3.0: Whats New With the 4.0?, Sep. 19, 2021, Publisher: Whoop.
https://fcc.report/FCC-ID/2AJ2X-WS30/4265060, FCC ID: 2AJ2X-WS30 External Photos of Whoop Strap 3.0, Nov. 4, 2019, Publisher: FCC.
https://fcc.report/FCC-ID/2AJ2X-WS30/4265061, FCC ID: 2AJ2X-WS30 Internal Photos of Whoop Strap 3.0, Nov. 4, 2019, Publisher: FCC.
Cancellation of DE202021004148U1 mailed May 4, 2023.
"https://www.apple.com/uk/newsroom/2018/09/redesigned-apple-watch-series-4-revolutionizes-comunication-fitness-and-health/'", Apple Watch Series 4: Beautifully redesigned with breakthrough communication, fitness and health capabilities (via WayBack Machine), Sep. 12, 2018, Publisher: apple.com.
Austad et al., An unobtrusive wearable device for ambulatory monitoring of Pulse Transit time to estimate Central Blood Pressure, Feb. 21, 2016, pp. 179-186, vol. 1, Publisher: Proceedings of the 9th International Joint Conference on Biomedical Engineering Systems and Technologies.
Chapman, Kathleen, "https://the-gadgeteer.com/2015/04/21/hahoo-fitness-tckr-x-review/'", Wahoo Fitness Tickr X review (via WayBack Machine), Apr. 21, 2015, Publisher: the Gadgeteer.
Crane, Lee, "https://www.digitaltrends.com/mobile/under-armour39-review/", Under Armour39 Review (via WayBack Machine), Jun. 21, 2013, Publisher: digitaltrends.com.
"https://www.dcrainmaker.com/2010/08/solution-to-heart-rate-dropoutspikes/html", A solution ot heart rate dropouts/spikes with Garmin HR Soft Straps, Aug. 22, 2010, Publisher: DC Rainmaker.

(56) References Cited

OTHER PUBLICATIONS

"https://www.dcrainmaker.com/2010/08/solution-to-heart-rate-dropoutspikes/html", Suunto Ambit3 Multisport GPS Watch In-Depth Review (via WayBack Machine), Sep. 29, 2014, Publisher: DC Rainmaker.

Duffy, Jill, "https://www.pcmag.com/reviews/mio-link", MIO Link Review, Apr. 16, 2014, Publisher: PCMag.com.

Duffy, Jill, Scosche Rhythm24 Review (via WayBack Machine), Dec. 12, 2019, Publisher: PCMag.com.

Duffy, Jill, Garmin HRM-Dual (via WayBack Machine), Oct. 8, 2019, Publisher: PCMag.com.

Duffy, Jill, The Best Heart Rate Monitors for 2020 (via WayBack Machine), Dec. 18, 2019, Publisher: PCMag. com.

Duffy, Jill, Wahoo Tickr X Heart Rate Monitor Review (via WayBack Machine), Dec. 18, 2019, Publisher: PCMag.com.

Hannam, Lisa, "https://www.besthealthmag.ca/article/smart-bra/#:~:text=Lol%C3%AB%20Smart%20Bra%2C%20%2490%20at,%2C%20%2495%20at%20lolewomen.com.", The Sports Bra That Tracks Your Heart Rate, May 29, 2017, Publisher: Best Health.

Isakeit et al., "https://www.ifixit.com/Teardown/Apple+Watch+Series+4+Teardown/113044", Apple Watch Series 4 Teardown, Sep. 24, 2018, Publisher: ifixit.com.

Lamkin, Paul, "https://www.wareable.com/smart-clothing/victorias-secret-sports-bra-heart-rate-monitor", Victoria's Secret Incredible bra wants a piece of your heart, Nov. 26, 2014, Publisher: Wareable.

Lamkin, Paul, Adidas miCoach Fit Smart review (via WayBack Machine), Nov. 5, 2015, Publisher: Wearable.

Lamkin, Paul, "https://www.wareable.com/sport/myzone-mz-3-review-3333", MyZone MZ-3 review (via WayBack Machine), Nov. 24, 2015, Publisher: Wearable.

Lamkin, Paul, "https://www.wareable.com/sport/myzone-training-top-wants-a-piece-of-your-heart-2457", MyZone connected t-shirt wants a piece of your heart, Mar. 15, 2016, Publisher: Wearable.

Lemay et al., "2.3 Application of Optical Heart Rate Monitoring", Wearable Sensors Fundamentals, Implementation and Applications, Aug. 14, 2014, pp. 105-129, Publisher: Academic Press, Sazonov & Neuman Eds., Published in: United States.

MIO Link Complete User Guide, Jan. 1, 2014, Publisher: mioglobal.com.

Nosowitz, Dan, "https://www.popsci.com/technology/article/2011-02/under-armours-sensor-embedded-shirts-measure-nfl-prospects-stride-stride/", Under Armours Sensor-Embedded Shirts Measure NFL Prospects, Stride by Stride (via WayBack Machine), Feb. 24, 2011, Publisher: Popular Science.

Sport Tester Heart Rate Monitor User's Instruction Manual GBR 175015.A, Jan. 1, 1993, Publisher: Polar.

Polar WearLink + Coded Transmitter 31 Coded Transmitter W.I.N.D. User Manual, Jan. 1, 2010, Publisher: Polar.

Polar H10 User Manual, Jan. 1, 2017, Publisher: Polar.

"https://www.polar.com/enivantage/m", Polar Vantage M (via WayBack Machine), Feb. 3, 2019, Publisher: Polar.com.

"https://www.prnewswire.com/news-releases/apple-watch-4s-ppg-and-ecg-health-sesors-2019-physical-manufacturer-process-cost-analysis-300911621.html", Apple Watch 4's PPG and ECG Health Sensors 2019: Physical, Manufacturer Process, Cost Analysis (via WayBack Machine), Sep. 4, 2019, Publisher: PR Newswire.

NuMetrex Adidas miCoach Mens Training Shirt, Short Sleeve (via WayBack Machine), Nov. 8, 2014, Publisher: Running Shoes Guru.

Sawh, Michael, "https://www.wareable.com/running/polar-vantage-m-review-6816", Polar Vantage M review, Dec. 18, 2018, Publisher: Wearable (via Wayback Machine).

"https://www.sportsbusinessjournal.com/Daily/Issues/2016/02/04/Technology/newly-launched-connected-sports-bra-will-get-you-in-shape.aspx", Newly Launched Connected Sports Bra Will Get You In Shape, Feb. 4, 2016, Publisher: Sports Business Journal.

Seeberg et al., A Novel Method for Continuous, Noninvasive, Cuff-Less Measurement of Blood Pressure: Evaluation in Patients With Nonalcoholic Fatty Liver Disease, Jul. 1, 2017, pp. 1469-1478, vol. 64, No. 7, Publisher: IEEE Trans Biomed Eng.

Song, Victoria, Polar H10 Heart Rate Sensor, Aug. 14, 2017, Publisher: PCMag.com.

Suunto Comfort Belt User Guide, Dec. 1, 2008, Publisher: Suunto.

Suunto Smart Sensor 1.1 User Guide, Mar. 1, 2015, Publisher: Suunto.

A39MIDT Strap & Module User Manual, Mar. 20, 2013, Publisher: Under Armour.

\* cited by examiner

WEARABLE ASSEMBLY COMPRISING A WEARABLE ARTICLE AND AN ELECTRONICS MODULE

CROSS-REFERENCE TO RELATED APPLICATIONS

This application is a Continuation of U.S. application Ser. No. 17/790,750 filed Jul. 4, 2022, which is herein incorporated by reference in its entirety, and which is a 371 National Phase entry of PCT/GB2021/050395 filed Feb. 18, 2021, which claims priority to GB 2002254.7 filed Feb. 19, 2020.

FIELD OF THE INVENTION

The present invention is directed towards a wearable assembly comprising a wearable article and an electronics module, and in particular towards an assembly comprising an electronics module with an internal sensor.

BACKGROUND

Wearable articles can be designed to interface with a wearer of the article, and to determine information such as the wearer's heart rate, rate of respiration, activity level, and body positioning. Such properties can be measured with a sensor assembly that includes a sensor for signal transduction and/or microprocessors for analysis. The articles include electrically conductive pathways to allow for signal transmission between an electronics module for processing and communication and sensing components of the article. The wearable articles may be garments. Such garments are commonly referred to as 'smart clothing' and may also be referred to as 'biosensing garments' if they measure biosignals.

It is desirable to overcome at least some of the problems associated with the prior art, whether explicitly discussed herein or otherwise.

SUMMARY

According to the present disclosure there is provided an electronics module and an apparatus as set forth in the appended claims. Other features of the invention will be apparent from the dependent claims, and the description which follows.

According to a first aspect of the disclosure, there is provided a wearable assembly comprising: a wearable article comprising a sensing component; an electronics module arranged to be removably coupled to the wearable article, the electronics module comprising: a housing; a processor disposed within the housing; an interface element arranged to interface with the sensing component of the wearable article so as to receive signals from the sensing component and provide the same to the processor; and a sensor disposed within the housing, the sensor being arranged to monitor a property of the environment external to the electronics module through the housing, wherein the housing is constructed such that the sensor has line of sight through the housing.

Advantageously, the electronics module comprises an interface element arranged to interface with a sensing component of the wearable article and further comprises a sensor for monitoring a property of the external environment through the housing such as via an opening in the housing. This enables the electronics module to perform monitoring through both sensing components (e.g. electrodes) of the wearable article as well as through an internal sensor. In some examples, the sensing component of the wearable article may be an electrode for monitoring an ECG signal of the wearer while the internal sensor for the electronics module may be an optical sensor arrangement to monitor PPG signals for the subject. The wearable assembly is thus able to perform the dual function of measuring ECG signals and PPG signals using a single electronics module.

Moreover, having the electronics module being able to perform monitoring via both sensing components of the wearable article and an internal sensor enables the electronics module to perform different types of monitoring operations depending on whether it is coupled to the wearable article. For example, when coupled to the wearable article, the electronics module is able to receive ECG signals which generally provide a greater accuracy in heart rate monitoring when compared to optical sensors, particularly when the wearer is moving. When decoupled from the wearable article, still able to receive PPG signals. This allows for continuous heart rate monitoring even when the user is not wearing the wearable article with the sensing components.

The wearable article may be a garment such as T-shirt with electrodes. During the day, the electronics module may be coupled to the garment to receive ECG signals (and PPG signals if desired at the same time). At night, the electronics module may be attached to a wrist-band to monitor PPG signals. This allows for continuous monitoring of the user during both day and night.

The sensing components are not required to be electrodes for measuring ECG signals. The sensor is not required to be an optical sensor. These are just examples.

The interface element may comprise a conductive material. The conductive material may provide a surface arranged to interface with a conductive region of the wearable article so as to conductively connect the electronics module to the conductive region of the wearable article.

The interface element may comprise a first conductive material and a second conductive material, wherein the first and second conductive materials are spaced apart from one another.

The sensor may be located between the first and second conductive materials.

The conductive material may form a contact pad.

The conductive material may be formed of a flexible conductive material.

The flexible conductive material may be a conductive elastomeric material.

Advantageously, the conductive material may be made of a conductive elastomer (e.g. a conductive rubber). A conductive elastomer is more user friendly and comfortable to touch than metallic conductive materials or hook and loop conductive fasteners. In addition, a conductive elastomer can be easier to wipe clean, is less likely to attract detritus or damage the conductive region of the wearable article due to repeated use.

The housing may comprise an opening aligned with the sensor such that the sensor has line of sight through the housing.

The housing may comprise a window aligned with the sensor such that the sensor has line of sight through the window. The window may be constructed from a transparent, translucent, or light-diffracting material.

The sensor may be arranged to monitor a property of the user wearing the wearable article.

The sensor may comprise one or more of an altitude sensor, optical sensor, pressure sensor, temperature sensor, humidity sensor, presence sensor, and air quality sensor.

The sensor may comprise an infrared temperature sensor arranged to measure the skin surface temperature of a user wearing the wearable article.

The sensor may comprise an optical sensor. The optical sensor may measure light in one or more of the infrared, visible, and ultraviolet spectrums. The optical sensor may be a pulse oximeter. The optical sensor may be arranged to measure the oxygen saturation of the wearer. Oxygen saturation is the fraction of oxygen-saturated haemoglobin relative to total haemoglobin (unsaturated+saturated) in the blood. The optical sensor may be arranged to measure the capillary perfusion of the wearer. A pulse oximeter may be useable to measure the capillary perfusion using a double-wavelength method. The capillary perfusion can be derived from a variation in the detected signal strength. The optical sensor may be arranged to measure the temperature of the wearer.

The electronics module may further comprise a light source disposed within the housing, the light source is arranged to emit light through the housing.

The wearable article may comprise an electronics module holder arranged to receive the electronics module. The electronics module holder may comprise a pocket. The pocket may be arranged to apply a compressive force to hold the electronics module in position within the pocket so as to communicatively couple the interface element to the sensing component of the wearable article.

The electronics module may further comprise a communicator arranged to communicate with an external device.

According to a second aspect of the disclosure, there is provided an electronics module for a wearable article. The electronics module comprises a rigid housing. The electronics module comprises an outer layer of flexible material covering at least part of the rigid housing.

Advantageously, the outer layer of flexible material provides a more visually pleasing outer appearance for the electronics module which is able to cover and hide manufacturing errors, markers or imperfections in the rigid housing. This helps increase manufacturing output and reduce waste as imperfect rigid housings do not need to be scrapped, and instead can still be utilised to form the electronics module. Moreover, the outer layer of flexible material is more user friendly and comfortable to touch.

Here, "rigid" will be understood as referring to a material which is stiffer and less able to bend than the outer layer of flexible material. The rigid housing may still have some degree of flexibility but is less flexible than the outer layer flexible material.

The outer layer of flexible material may provide a gripping surface arranged to interface with the wearable article so as to restrict movement of the electronics module relative to the wearable article.

The outer layer of flexible material may be constructed form a textile material. The textile material may comprise a woven fabric material. The woven fabric material may comprise an open weave.

The electronics module may further comprise an electronics component.

The outer layer of flexible material may at least partially cover the electronics component. The outer layer of flexible material may be constructed such that the electronics component has line-of-sight through the outer layer of flexible material.

The electronics component may be disposed within the rigid housing. The rigid housing may be constructed such that the electronics component has line of sight through the rigid housing.

The rigid housing may comprise an opening aligned with the electronics component such that the electronics component has line of sight through the rigid housing.

The rigid housing may comprise a window aligned with the electronics component such that the electronics component may have line of sight through the window. The window may be constructed from a transparent, translucent, or light-diffracting material.

The outer layer of flexible material may be constructed such that the electronics component has line-of-sight through the outer layer of flexible material. The outer layer of flexible material may cover the rigid housing in the vicinity of the electronics component. The outer layer of flexible material may cover the opening or window of the housing.

The electronics component may be located on an outside surface of the rigid housing. The electronics component may be a capacitive sensor, for example. The outer layer of flexible material may cover the electronics component. The outer layer of flexible material may be constructed such that the electronics component has line-of-sight through the outer layer of flexible material.

The electronics component may comprise a sensor arranged to monitor a property of the environment external to the electronics module through the outer layer of flexible material. The property may be a property of the user wearing the wearable article.

The sensor may comprise one or more of an altitude sensor, pressure sensor, temperature sensor, optical sensor, humidity sensor, presence sensor, and air quality sensor. The presence sensor may for detecting a touch input from a user. The presence sensor may comprise one or more of a capacitive sensor, inductive sensor, and ultrasonic sensor.

The sensor may comprise an infrared temperature sensor arranged to measure the skin surface temperature of a user wearing the wearable article. The temperature sensor may be an ambient temperature sensor.

The electronics component may comprise a light source arranged to emit light which is visible through the outer layer of flexible material.

The housing may comprise a (rigid) polymeric material. The polymeric material may be a rigid plastic material. The rigid plastic material may be ABS or polycarbonate plastic, but is not limited to these examples. The rigid plastic material may be glass reinforced. The rigid housing may be injection moulded. The rigid housing may be constructed using a twin-shot injection moulding approach.

The rigid housing may comprise a top enclosure and a bottom enclosure. The top enclosure and the bottom enclosure may be joined together by a snap-fit mechanism. Alternatively or additionally, the top enclosure and the bottom enclosure may be joined together by screws, sonic welding, glue or by any other means known to those skilled in the art.

A sealing material such as a silicone bead may be applied to the rim of one or both of the top and bottom enclosures of the rigid housing such that when the top and bottom enclosures of the rigid housing are connected together, the sealing material seals the housing and prevents against water ingress. The unit may be assembled to enable waterproofing in another fashion.

The outer layer of flexible material may extend at least partially into the rigid housing. The outer layer of flexible material may be clamped between the top enclosure and the bottom enclosure of the rigid housing.

The outer layer of flexible material may cover at least part of the top enclosure of the rigid housing. The outer layer of flexible material may cover all of the top enclosure. The outer layer of flexible material may cover at least part of the bottom enclosure of the rigid housing. The outer layer of flexible material may cover all of the bottom enclosure.

The outer layer of flexible material may cover a substantial part of the rigid housing. The outer layer of flexible material may cover 20% or more of the rigid housing. The outer layer of flexible material may cover 30% or more of the rigid housing. The outer layer of flexible material may cover 40% or more of the rigid housing. The outer layer of flexible material may cover 50% or more of the rigid housing. The outer layer of flexible material may cover 60% or more of the rigid housing. The outer layer of flexible material may cover 70% or more of the rigid housing. The outer layer of flexible material may cover 80% or more of the rigid housing. The outer layer of flexible material may cover 90% or more of the rigid housing. The outer layer of flexible material may cover the entirety of the rigid housing.

The electronics module may comprise a processor disposed within the rigid housing. The processor may be arranged to receive signals from a sensing component. The sensing component may be a component of the electronics module or the wearable article. The electronics module may further comprise an interface element arranged to interface with a sensing component of the wearable article. The processor may be arranged to receive signals from the sensing component of the wearable article via the interface.

The electronics module may further comprise a communicator arranged to communicate with an external device.

The outer layer of flexible material may function as a capacitive sensor for the electronics module. This enables the outer layer of flexible material to function as a touch sensor. One or a plurality of electronics components may be provided under the outer layer of flexible material and outside of the rigid housing. The plurality of electronics components may function as capacitive touch sensors.

The outer layer of flexible material may be adhered to the rigid housing using a suitable adhesive. The outer layer of flexible material may be welded to the rigid housing. The outer layer of flexible material may be clamped between top and bottom enclosures of the rigid housing. That is, part of the outer layer of flexible material may extended into the internal space of the rigid housing such that, when the top enclosure of the rigid housing is brought into contact with the bottom enclosure of the rigid housing, the top and bottom enclosures press against the outer layer of flexible material and hold it in place. An adhesive may be applied to the flexible material at a location which is pressed between the top and bottom enclosures. This location may correspond to the outer edge of the flexible material. Adhesive may not be applied to other areas of the flexible material such as the areas of the flexible material which cover at least part of the top and/or bottom enclosure. Beneficially, an absence of adhesive on the external surface of the housing helps keep the fabric soft and avoids visible dried glue sections on the outside surface of the electronics module.

The electronics module may comprise a plurality of electronics components. Some or all of the electronics components may perform different functions and may be located within or outside of the rigid housing.

The outer layer of flexible material may comprise a flexible conductor. The flexible conductor may provide a surface arranged to interface with a conductive region of the wearable article so as to conductively connect the electronics module to the conductive region of the wearable article.

The outer layer of flexible material may provide a gripping surface arranged to interface with the wearable article so as to restrict movement of the electronics module relative to the wearable article.

The surface of the flexible conductor may provide the gripping surface.

The flexible conductor may comprise a conductive textile. The flexible conductor may comprise a conductive fabric material.

The outer layer of flexible material may comprise a textile material. The outer layer of textile material may comprise a fabric material, optionally a woven fabric material.

The outer layer of flexible material may comprise an elastomeric material. The flexible conductor may comprise a conductive elastomeric material.

The flexible conductor may comprise a 2D electrically conductive material such as graphene. The flexible conductor may comprise a mixture or composite of an elastomeric material and a 2D electrically conductive material.

The surface of the flexible conductor may be generally planar.

The outer layer of flexible material may comprise a first flexible conductor and a second flexible conductor. The first flexible conductor and the second flexible conductor may be spaced apart from one another. The outer layer of flexible material may comprise more than two flexible conductors. Each of the flexible conductors may be spaced apart from one another to define multiple conductive regions.

The outer layer of flexible material may further comprise a non-conductive region that separates the first flexible conductor from the second flexible conductor.

The flexible conductor may be electrically connected to an electronics component within the housing.

The flexible material may extend into the rigid housing and may be electrically connected to the electronics component within the housing by a conductor.

The flexible conductor may be electrically connected to an electronics component within the housing by a conductor that extends from the electronics component to the flexible conductor through an opening in the rigid housing.

The opening in the rigid housing may be sealed by the flexible conductor.

The conductor may be a forced biased conductor. The conductor may be a spring-loaded pin.

The outer layer of fabric material may be adhered to the rigid housing.

According to a third aspect of the disclosure, there is provided an electronics module for a wearable article. The electronics module comprises a housing. The electronics module comprises an electronics component disposed within the housing. The housing is constructed such that the electronics component has line of sight through the housing.

Advantageously, the housing is constructed such that it provides line of sight for an electronics component disposed within the housing. This allows the electronics component to interact with the environment external to the electronics module from within the module. For example, the present disclosure allows for a sensor to monitor the external environment from within the electronics module. In another example, the present disclosure allows for a light source to emit light which is visible externally.

According to a fourth aspect of the disclosure, there is provided an electronics module for a wearable article. The electronics module comprises a flexible material covering at least part of an external surface of the electronics module. The flexible material comprises a flexible conductor. The flexible conductor provides a surface arranged to interface with a conductive region of the wearable article so as to conductively connect the electronics module to the conductive region of the wearable article.

Advantageously, the electronics module comprises a flexible conductor covering part of an external surface of the electronics module. Use of a flexible conductor avoids the need of rigid metallic conductors on the electronics module.

According to a fifth aspect of the disclosure, there is provided an electronics module for a wearable article. The electronics module comprises a housing. The electronics module comprises an electronics component disposed within the housing. The electronics module comprises a conductive material covering at least part of an external surface of the housing. The electronics module comprises a conductor extending through an opening in the housing to conductively connect the electronics component to the conductive material. The conductive material provides a surface arranged to interface with a conductive region of the wearable article so as to conductively connect the electronics module to the conductive region of the wearable article.

Advantageously, the electronics module comprises a housing and a conductive material covering at least part of the external surface of the housing. This means that the housing and conductive material can be manufactured separately and at separate locations and subsequently assembled together. This simplifies the manufacturing process. In existing approaches, the conductive materials is first attached to the electronics component and then the housing is formed by overmoulding. The conductive material may be a rigid or a flexible conductive material.

According to a sixth aspect of the present disclosure, there is provided a method of constructing an electronics module for a wearable article. The method comprises providing a housing comprising an electronics component disposed within the housing, and a conductor extending from the electronics component and through an opening in the housing. The method comprises attaching a conductive material to an external surface of the housing such that it covers at least part of an external surface of the housing and is conductively connected to the conductor.

According to a seventh aspect of the present disclosure, there is provided an electronics module for a wearable article. The electronics module comprises an electronics component. The electronics module comprises a force-biased conductor extending from the electronics component. The electronics module comprises a conductive material, wherein the force-biased conductor is urged against the conductive material so as to conductively connect the electronics component to the conductive material.

The conductive material provides a surface arranged to interface with a conductive region of the wearable article so as to conductively connect the electronics module to the conductive region of the wearable article.

Advantageously, the electronics module of the present disclosure is able to electrically conductively connect an electronics component to a conductive material without requiring that the conductive material is soldered, welded or otherwise fixedly connected to the conductor. This simplifies the manufacturing process. The conductive material may be a rigid or a flexible conductive material.

The electronics module of the third, fourth, fifth or seventh aspect of the disclosure may comprise some or all of the features of the electronics module of the second aspect of the disclosure and vice versa. Any of the electronics modules according to these aspects may be useable in the wearable assembly of the first aspect of the disclosure.

According to an eighth aspect of the present disclosure, there is provided a method of constructing an electronics module for a wearable article. The method comprises providing an electronics component and a force-biased conductor extending from the electronics component. The method comprises providing a conductive material, wherein the conductive material provides a surface arranged to interface with a conductive region of the wearable article. The method comprises applying pressure to the force-biased conductor so as to urge the force-biased conductor against the conductive material to form a conductive connection.

According to a ninth aspect of the disclosure, there is provided an apparatus. The apparatus comprises an electronics module according to any of the aspects of the disclosure. The apparatus further comprises a wearable article comprising a conductive region, wherein the conductive material of the electronics module is arranged to interface with the conductive region of the wearable article so as to conductively connect the electronics module to the conductive region of the wearable article.

The wearable article may be a garment.

The wearable article may further comprise a sensing component, and optionally an electrically conductive pathway extending from the sensing component to the conductive region of the wearable article.

The wearable article may comprise one or more sensing components. The sensing components may be biosensing components. The sensing components may comprise one or more components of a temperature sensor, a humidity sensor, a motion sensor, an electropotential sensor, an electroimpedance sensor, an optical sensor, an acoustic sensor. Here, "component" means that not all of the components of the sensor may be provided in the wearable article. The processing logic, power and other functionality may be provided in the electronics module. The wearable article may only comprise the minimal functionality to perform the sensing such as by only including sensing electrodes. The temperature sensor may be arranged to measure an ambient temperature, a skin temperature of a human or animal body, or a core temperature of a human or animal body. The humidity sensor may be arranged to measure humidity or skin-surface moisture levels for a human or animal body. The motion sensor may comprise one or more of an accelerometer, a gyroscope, and a magnetometer sensor. The motion sensor may comprise an inertial measurement unit. The electropotential sensor may be arranged to perform one or more bioelectrical measurements. The electropotential sensor may comprise one or more of electrocardiography (ECG) sensor modules, electrogastrography (EGG) sensor modules, electroencephalography (EEG) sensor modules, and electromyography (EMG) sensor modules. The electroimpedance sensor may be arranged to perform one or more bioimpedance measurements. Bioimpedance sensors can include one or more of plethysmography sensor modules (e.g., for respiration), body composition sensor modules (e.g., hydration, fat, etc.), and electroimpedance tomography (EIT) sensors. An optical sensor may comprise a photoplethysmography (PPG) sensor module or an orthopantomogram (OPG) sensor module.

The present disclosure is not limited to wearable articles. The electronics arrangement disclosed herein may be incorporated into other forms of devices such as user electronic devices (e.g. mobile phones). In additions, they may be incorporated into any form of textile article. Textile articles may include upholstery, such as upholstery that may be positioned on pieces of furniture, vehicle seating, as wall or ceiling décor, among other examples.

BRIEF DESCRIPTION OF THE DRAWINGS

Examples of the present disclosure will now be described with reference to the accompanying drawings, in which.

DETAILED DESCRIPTION

Figure 1:
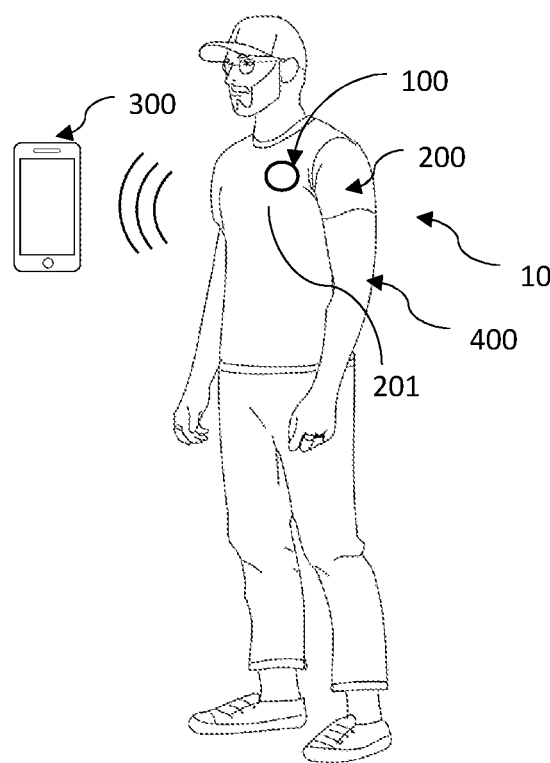
FIG. 1 shows a schematic diagram for an example system according to aspects of the present disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of electronic device which may be worn by a user such as a smart watch, necklace, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, swimwear, personal protection equipment, wetsuit or drysuit.

The wearable article/garment may be constructed from a woven or a non-woven material. The wearable article/garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment.

The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment. The present disclosure is not limited to wearable articles for humans and includes wearable articles for animals such as animal collars, jackets and sleeves.

The following description refers to particular examples of the present disclosure where the wearable article is a garment. It will be appreciated that the present disclosure is not limited to garments and other forms of wearable article are within the scope of the present disclosure as outlined above.

Referring to FIG. 1, there is shown an example system 10 according to aspects of the present disclosure. The system 10 comprises an electronics module 100, a garment 200, and a mobile device 300. The electronics module 100 and garment 200 form a wearable assembly. The garment 200 is worn by a user 400. The electronics module 100 is attached to the garment 200. The electronics module 100 is shown on the outside surface 201 of the garment 200 in FIG. 1 but may also be within the garment 200 or hidden within an external pocket or similar mounting arrangement of the garment 200.

The electronics module 100 is arranged to integrate with sensing components incorporated into the garment 200 so as to obtain signals from the sensing components. The sensing components may comprise electrodes. The electronics module 100 is further arranged to wirelessly communicate data to the mobile device 300. Various protocols enable wireless communication between the electronics module 100 and the mobile device 300. Example communication protocols include Bluetooth®, Bluetooth® Low Energy, and near-field communication (NFC). In some examples, the electronics module 100 may communicate over a long-range wireless communication protocol.

The electronics module 100 may be removable from the garment 200. The mechanical coupling of the electronic module 100 to the garment 200 may be provided by a mechanical interface such as a clip, a plug and socket arrangement, etc. The mechanical coupling or mechanical interface may be configured to maintain the electronic module 100 in a particular orientation with respect to the garment 200 when the electronic module 100 is coupled to the garment 200. This may be beneficial in ensuring that the electronic module 100 is securely held in place with respect to the garment 200 and/or that any electronic coupling of the electronic module 100 and the garment 200 (or a component of the garment 200) can be optimized. The mechanical coupling may be maintained using friction or using a positively engaging mechanism, for example.

Beneficially, the removable electronics module 100 may contain all of the components required for data transmission and processing such that the garment 200 only comprises the sensor components and communication pathways. In this way, manufacture of the garment 200 may be simplified. In addition, it may be easier to clean a garment 200 which has fewer electronic components attached thereto or incorporated therein. Furthermore, the removable electronics module 100 may be easier to maintain and/or troubleshoot than embedded electronics. The electronic module 100 may comprise flexible electronics such as a flexible printed circuit (FPC). The electronic module 100 may be configured to be electrically coupled to the garment 200.

It may be desirable to avoid direct contact of the electronics module 100 with the wearer's skin while the garment 200 is being worn. It may be desirable to avoid the electronics module 100 coming into contact with sweat or moisture on the wearer's skin or other sources of moisture such as from rain or a shower. It may further be desirable to provide an electronics module holder such as a pocket in the garment to contain the electronics module 100 in order to prevent chafing or rubbing and thereby improve comfort for the wearer. The pocket may be provided with a waterproof lining in order to prevent the electronic module 100 from coming into contact with moisture.

Figure 2:
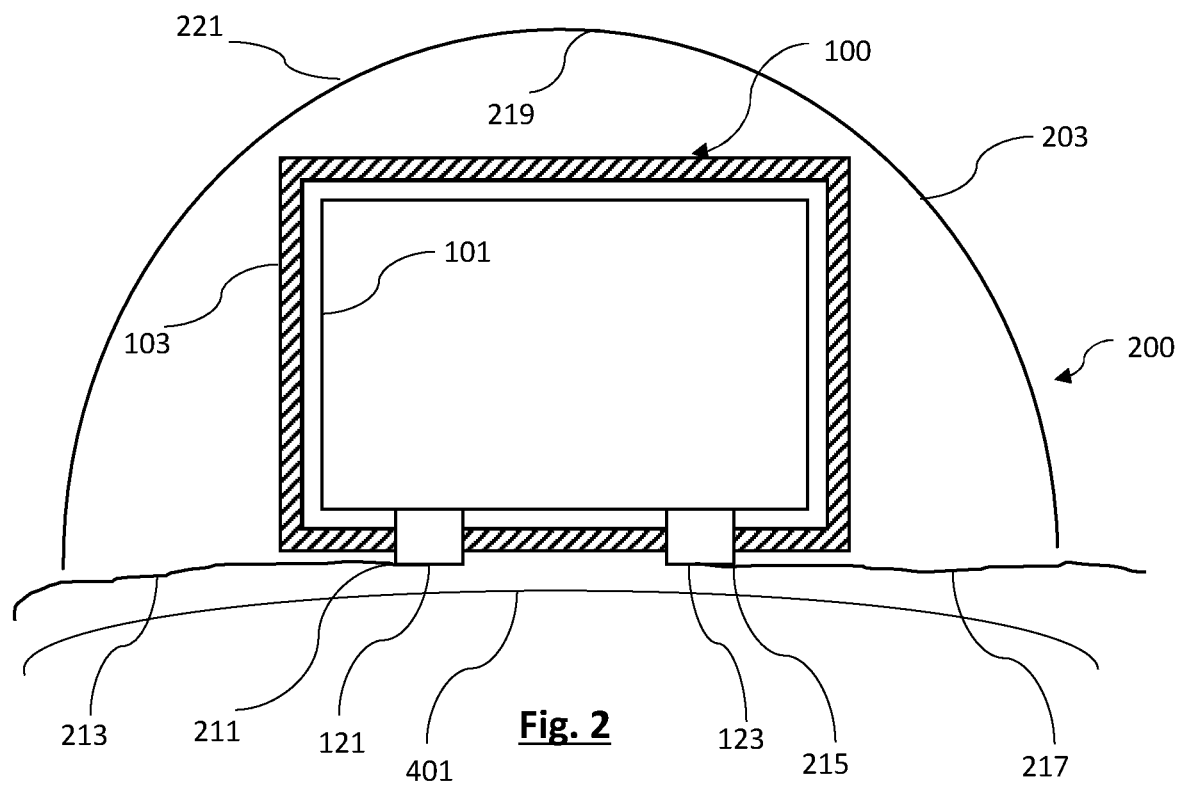
FIG. 2 shows a sectional view of an example apparatus comprising an electronics module and a wearable article according to aspects of the present disclosure.

Referring to FIG. 2, there is shown a sectional view of an apparatus comprising a garment 200 and an electronics module 100 disposed within an electronics module holder 203 of the garment 200. The garment 200 is being worn by a user and is proximate to the skin surface 401 of the user.

The electronics module holder 203 in this example is an elasticated pocket 203 positioned on the outside surface of the garment 200. In other examples, the electronics module holder 203 may be provided within the garment 200 such as in the form of an inner pocket.

The pocket 203 allows the user to position the electronics module 100 in the pocket 203 and remove it therefrom. The pocket 203 applies a compressive force to help hold the electronics module 100 in a generally fixed position within the pocket 203. This is not required in all examples as gripping surfaces of the electronics module 100 and/or the garment 200/pocket 203 may be sufficient for limiting relative movement between the electronics module 100 and the garment 200. Additionally or separately, the electronics module 100 and the garment 200 may comprise magnetic elements to help hold the electronics module 100 in a fixed position relative to the garment 200. The housing of the electronics module 100 may be constructed to enable a magnet to be retained therein. In particular, a recess may be provided in an inner surface of a bottom enclosure of an electronics module 100 sized to retain a magnet.

The pocket 203 comprises a layer of material 203 which is bonded, stitched, otherwise attached to or integrally formed with the garment 200. The pocket 203 has an inner surface 219 facing the electronics module 100. The pocket 203 has an outer surface 221 which can be considered as part of the outer surface 201, 221 of the garment 200.

In some examples, the inner surface 219 of the pocket 203 may be provided with a surface which increases friction between the inner surface 219 and the electronics module 100 when positioned in the pocket 203. The surface may comprise a number of horizontal lines or dots of gripping material provided on the inner surface 219. The gripping material may be a silicone-based coating. The surface helps reduce unnecessary rotational or translational movement of the electronics module 100 when positioned in the pocket 203 and helps maintain the interface of the electronics module 100 in contact with the terminal regions 211, 215 of the garment 200.

The electronics module 100 comprises a rigid housing 101. One or more electrical components are provided within the rigid housing 101. An outer layer of flexible material 103 covers at least part of the rigid housing 101. The outer layer of flexible material 103 provides a more visually pleasing outer appearance for the electronics module 100 which is able to cover and hide manufacturing errors, markers or imperfections in the rigid housing 101. Beneficially, this helps increase manufacturing output and reduce waste as imperfect rigid housings 101 do not need to be scrapped, and instead can still be utilised to form the electronics module 100.

Moreover, the outer layer of flexible material 103 is more user friendly and comfortable to touch and so is easier for the user to manipulate and position/remove from the pocket 203.

Furthermore, the outer layer of flexible material 103 provides a gripping surface which interfaces with the lining of the pocket 203 so as to help hold the electronics module 100 in place in the pocket 203. The gripping surface may be an abrasive surface.

In the example of FIG. 2, the outer layer of flexible material 103 is constructed from a textile material, and in particular a woven fabric material that uses an open weave. The open weave provides an abrasive/gripping surface for gripping against the pocket 203/garment 200. In addition, the open weave may facilitate heat dissipation from the electronics module 100. Furthermore, the open weave allows for electrical components of the electronics module 100 to have a clear line-of sight through the outer layer of flexible material 103. The outer layer of flexible material 103 is not required to be a textile material. The outer layer of flexible material 103 may, for example, be a waterproof layer of material such as an elastomeric material (e.g. a rubber or silicone rubber casing).

The present disclosure is not limited to any particular form of fabric material with an open weave. In some examples, the fabric material may be similar to open weave fabric materials used in speakers or acoustic panels. This fabric material is typically a polyester mix fabric formed into a loose weave that has a grid line appearance.

Generally, the fabric material may be any woven or non-woven material. The fabric material may comprise natural fibres, synthetic fibres, or a natural fibre blended with one or more other materials which can be natural or synthetic. The yarn may be cotton. The cotton may be blended with polyester and/or viscose and/or polyamide. Silk may also be used as the natural fibre. Cellulose, wool, hemp and jute are also natural fibres that may be used in the fabric material. Polyester, polycotton, nylon and viscose are synthetic fibres that may be used in the fabric material.

The electronics module 100 comprises an interface in the form of electrical contacts 121, 123 that extend through the outer layer of fabric material 103. The first electrical contact 121 conductively connects with a first terminal region 211 of the garment 200. The first terminal region 211 enables the electronics module 100 to conductively connect to sensing components of the garment 200 via first electrically conductive pathway 213 of the garment 200. The sensing components may be one or more electrodes. The second electrical contact 123 conductively connects with a second terminal region 215 of the garment 200. The second terminal region 215 enables the electronics module 100 to conductively connect to sensing components of the garment 200 via second electrically conductive pathway 217 of the garment 200. The sensing components may be one or more electrodes.

In examples of the present disclosure, the electrical contacts 121, 123 may be in the form of conductive pads 121, 123. The conductive pads 121, 123 may have a generally planar shape or may have a textured surface.

Figure 3:
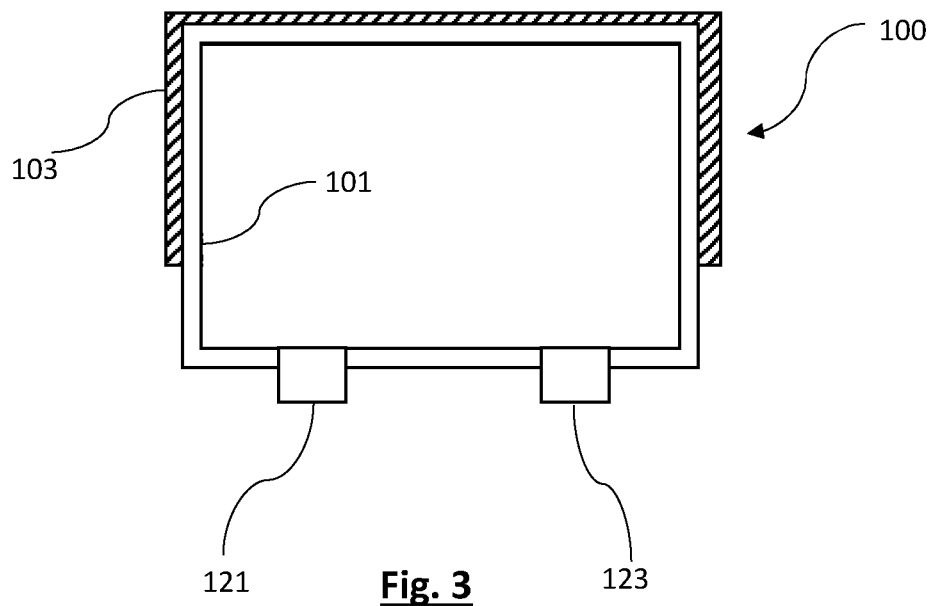
FIG. 3 shows a schematic diagram for an example electronics module according to aspects of the present disclosure.

Referring to FIG. 3, there is shown a schematic diagram of another example electronics module 100 according to aspects of the present disclosure. In this example, the outer layer of flexible material 103 does not cover the entirety of rigid housing 101 and instead covers the top of the rigid housing 101 and leaves the bottom of the rigid housing 101 uncovered.

Figure 4:
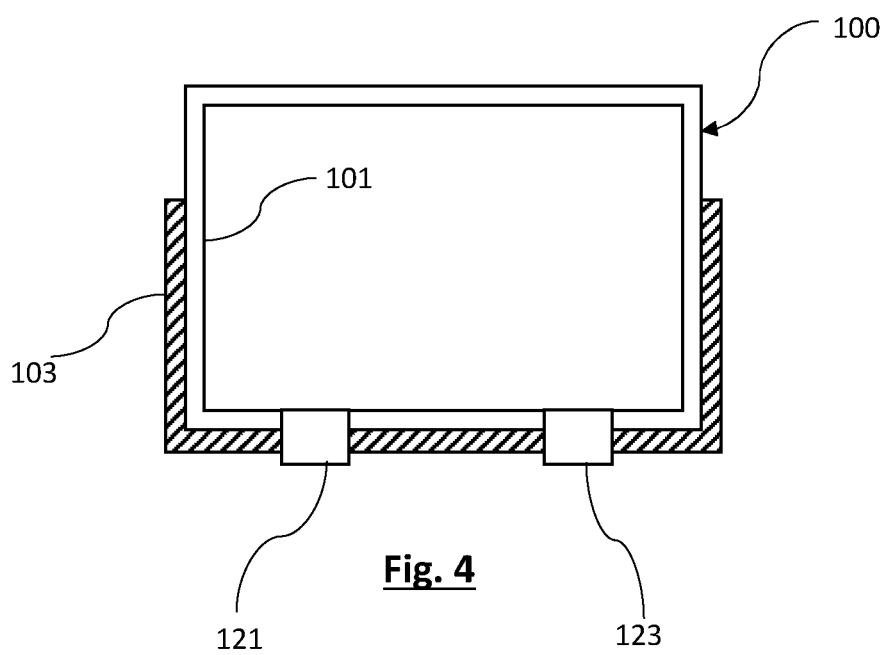
FIG. 4 shows a schematic diagram for another example electronics module according to aspects of the present disclosure.

Referring to FIG. 4, there is shown a schematic diagram of another example electronics module 100 according to aspects of the present disclosure. In this example, the outer layer of flexible material 103 does not cover the entirety of the rigid housing 101 and instead covers the bottom of the rigid housing 101 and leaves the top of the rigid housing 101 uncovered.

The examples of FIGS. 3 and 4 show that the outer layer of flexible material 103 is not required to completely cover the rigid housing 101 and benefits such as improved appearance, user experience and enabling gripping the electronics module holder 203 (amongst others) can be achieved using a partial covering of the rigid housing with the outer layer of flexible material 103.

Figure 5:
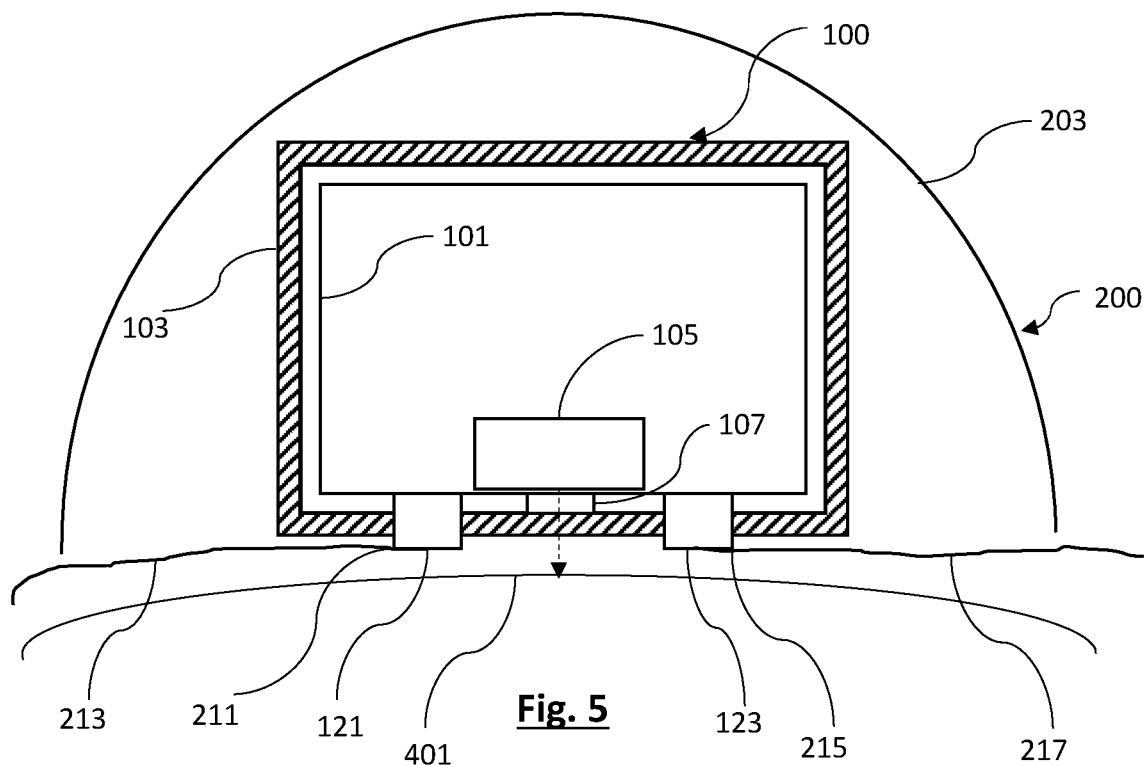
FIG. 5 shows a sectional view of another example apparatus comprising an electronics module and a wearable article according to aspects of the present disclosure.

Referring to FIG. 5, there is shown another example apparatus according to aspects of the present disclosure. The apparatus is similar to the apparatus of FIG. 2 and like reference numerals are used to indicate like components. The electronics module 100 further comprises an electronics component 105. The electronics component 105 is disposed within the rigid housing 101. The electronics component 105 is disposed proximate to a bottom surface of the electronics module 100 which is proximate to the skin surface 401 of the user wearing the garment 200. The rigid housing 101 comprises an opening 107 in the bottom surface through which the electronics component 105 has line of sight. The outer layer of flexible material 103 at least partially covers the opening 107 in the rigid housing 101. The outer layer of flexible material 103 is constructed such that the electronics component 105 has line-of-sight through the outer layer of flexible material 103. This can be achieved by the outer layer of flexible material having, for example, an open weave construction or by providing openings or windows in the outer layer of flexible material 103.

Figure 6:
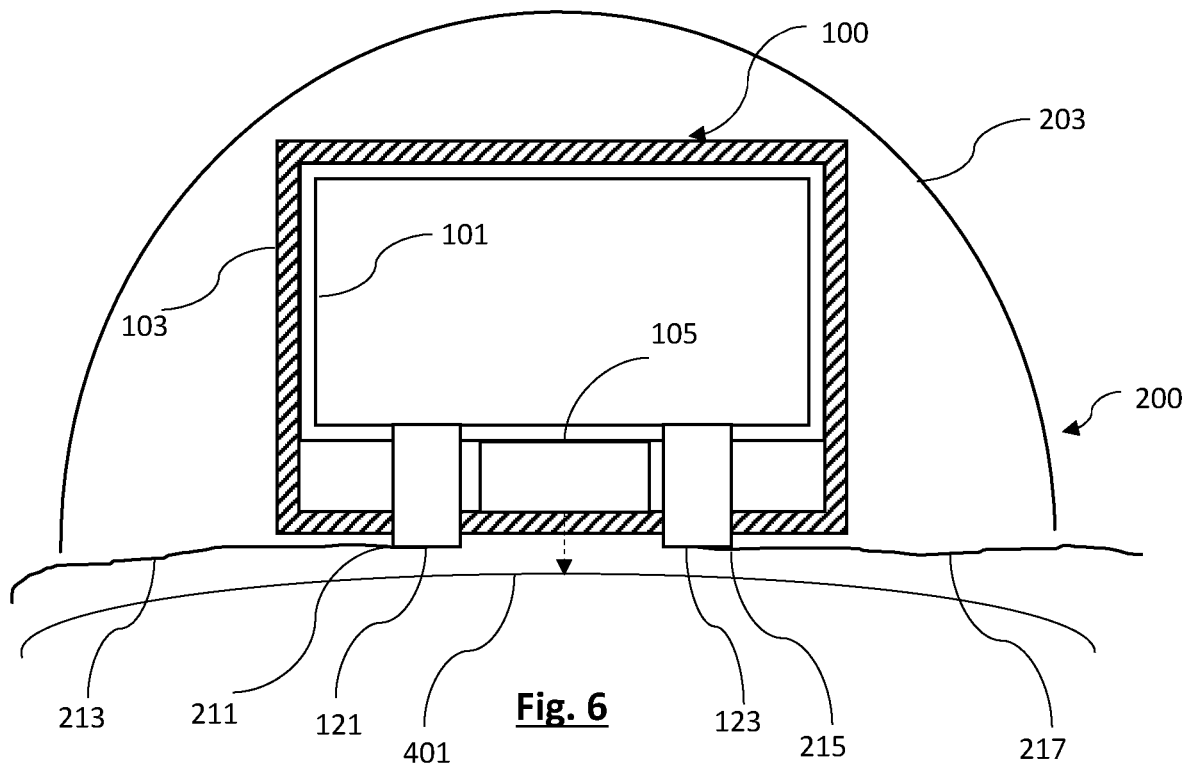
FIG. 6 shows a sectional view of yet another example apparatus comprising an electronics module and a wearable article according to aspects of the present disclosure.

Referring to FIG. 6, there is shown another example apparatus according to aspects of the present disclosure. The apparatus is similar to the apparatus of FIG. 2 and like reference numerals are used to indicate like components. The electronics module 100 further comprises an electronics component 105. The electronics component 105 is attached to the bottom external surface of the rigid housing 101 and is not provided in the rigid housing 101. The electronics component 105 is disposed proximate to a bottom surface of the electronics module 100 which is proximate to the skin surface 401 of the user wearing the garment 200. The outer layer of flexible material 103 at least partially covers electronics component 105. The outer layer of flexible material 103 is constructed such that the electronics component 105 has line-of-sight through the outer layer of flexible material 103. This can be achieved by the outer layer of flexible material 103 having, for example, an open weave construction or by providing openings in the outer layer of flexible material 103.

In the examples of FIGS. 5 and 6, the electronics component 105 of the electronics module 100 is arranged to have line-of-sight through the outer layer of flexible material 103 so that it may interact with the skin surface 401 of the user wearing the garment 200. This is particularly suited for examples where the electronics component is a sensor 105 arranged to monitor a property of the user. The sensor 105 may be, for example, a temperature sensor 105 arranged to monitor a core body temperature or skin-surface temperature of the user. The sensor 105 may be, for example, a humidity sensor 105 arranged to monitor a hydration or sweat level of the user.

In an example, the sensor 105 is a temperature sensor 105 arranged to measure the non-contact skin temperature of the user wearing the garment 200. The temperature sensor 105 may, in particular, be an infrared thermometer 105. The garment 200 in the region of the electronics module holder 203 may also have an opening, window or an open weave to help enable the infrared thermometer 105 record an accurate skin temperature.

In another example, the sensor 105 is a pulse oximeter arranged to measure the oxygen saturation and/or capillary perfusion of the user wearing the garment.

Figure 7:
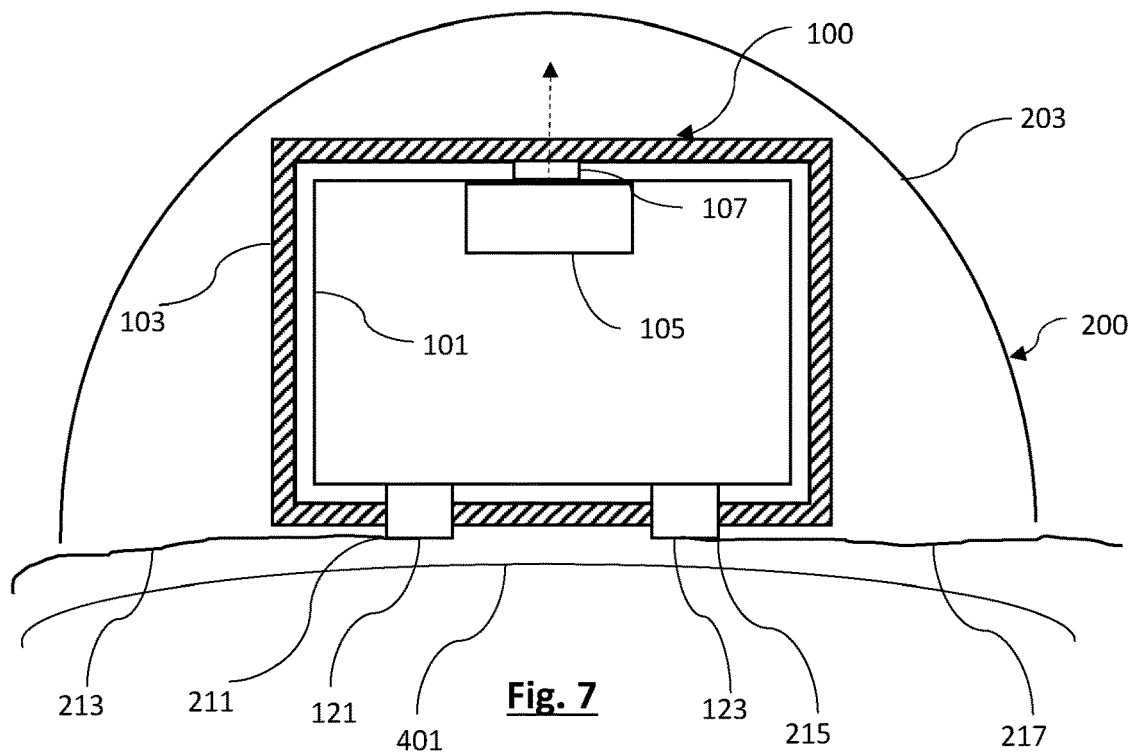
FIG. 7 shows a sectional view of yet another example apparatus comprising an electronics module and a wearable article according to aspects of the present disclosure.

Referring to FIG. 7, there is shown another example apparatus according to aspects of the present disclosure. The apparatus is similar to the apparatus of FIG. 2 and like reference numerals are used to indicate like components. The electronics module 100 further comprises an electronics component 105. The electronics component 105 is disposed within the rigid housing 101. The electronics component 105 is disposed proximate to a top surface of the electronics module 100 which is furthest from the skin surface 401 of the user wearing the garment 200. The rigid housing 101 comprises an opening 107 in the top surface through which the electronics component 105 has line of sight. The outer layer of flexible material 103 at least partially covers the opening 107 in the rigid housing 101. The outer layer of flexible material 103 is constructed such that the electronics component 105 has line-of-sight through the outer layer of flexible material 103. This can be achieved by the outer layer of flexible material having, for example, an open weave construction or by providing openings in the outer layer of flexible material 103.

In the examples of FIG. 7, the electronics component 105 of the electronics module 100 is arranged to have line-of-sight through the outer layer of flexible material 103 so that it may interact with the environment external to the user wearing the garment 200. This is particularly suited for examples where the electronics component is a sensor 105 arranged to monitor a property of the environment external to the user. In these examples, the sensor 105 may, for example, be one or of an altitude sensor (e.g. an altimeter), a pressure sensor (e.g. a barometer), a humidity sensor, or an air quality sensor. In other examples, the sensor 105 may be arranged to monitor a user interaction with the electronics module 100. The sensor 105 may, for example, be a presence sensitive sensor such as a capacitive sensor, inductive sensor or ultrasonic sensor.

In some examples, the electronics component 105 comprises a light source 105 which is arranged to emit light through the outer layer of flexible material so that it is visible externally. The light source 105 may comprise one or more light emitting diodes.

The garment 200 may also be constructed so that the electronics component 105 has line of sight through the garment 200. In the examples of FIGS. 5 and 6, the garment 200 is constructed such that the electronics component has line of sight with the skin surface 401 of the wearer of the garment 200. In the example of FIG. 7, the electronics module holder 203 is constructed such that the electronics component 105 has line of sight through the electronics module holder 203.

In some examples, the garment 200 being constructed to enable the electronics component 105 to have line of sight therethrough may mean that the garment 200 comprises an opening. The opening may extend from an inner surface to an outer surface of the garment 200. The opening is positioned such that, when the electronics module 100 is provided in the electronics module holder 203, the electronics component 105 is aligned with the opening. The opening may be formed by removing material from the layer of material of the electronics module holder 203 or the layer of material may be formed to include the opening during manufacture.

Rather than providing an opening in the material of the garment 200, a window may instead be provided. The window may be constructed from a transparent, translucent, or light diffracting material. The use of a light diffracting material may provide a light pipe effect to help the light source appear bigger than they are. In other examples, the material of the electronics module holder 203 may have an open-cell construction in the vicinity of the electronics component 105, when positioned in the electronics module holder 203, such that the electronics component 105 has line of sight through the garment 200.

Figure 8:
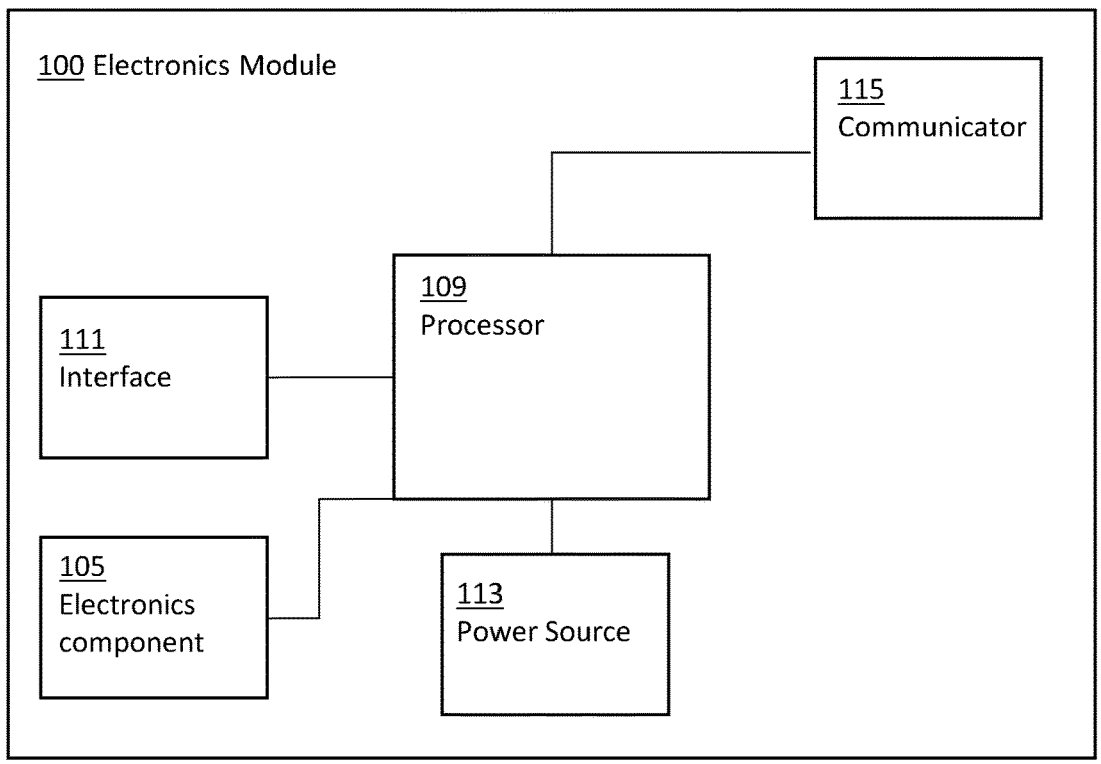
FIG. 8 shows a schematic diagram for another example electronics module according to aspects of the present disclosure.

Referring to FIG. 8, there is shown a schematic diagram for an example electronics module 100 according to aspects of the present disclosure.

The electronics module 100 comprises a processor 109 configured to process signals sensed by a sensing component of the electronics module 100 and/or the garment 200. The signals relate to the activity of a user wearing the garment 200.

The electronics module 100 comprises an electronics component 105. The electronics component 105 may comprise a light source or sensor as described above. The light source may be arranged to emit light to indicate a status of the electronics module or a property of a user wearing the wearable article, for example.

The electronics module 100 comprises a power source 113. The power source 113 is coupled to the processor 109 and is arranged to supply power to the processor 109. The power source 113 may comprise a plurality of power sources. The power source 113 may be a battery. The battery may be a rechargeable battery. The battery may be a rechargeable battery adapted to be charged wirelessly such as by inductive charging. The power source 113 may comprise an energy harvesting device. The energy harvesting device may be configured to generate electric power signals in response to kinetic events such as kinetic events performed by a wearer of the garment. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the garment. The energy harvesting device may be a thermoelectric energy harvesting device. The power source may be a super capacitor, or an energy cell.

The power source 113 in this example is a lithium polymer battery 113. The battery 113 is rechargeable and charged via a USB C input of the electronics module 100. Of course, the present disclosure is not limited to recharging via USB and instead other forms of charging such as inductive of far field wireless charging are within the scope of the present disclosure. Additional battery management functionality is provided in terms of a charge controller, battery monitor and regulator. These components may be provided through use of a dedicated power management integrated circuit (PMIC). The processor 109 is communicatively connected to the battery monitor such that the processor 109 may obtain information about the state of charge of the battery 113.

The communicator 115 may be a mobile/cellular communicator operable to communicate the data wirelessly via one or more base stations. The communicator 115 may provide wireless communication capabilities for the garment 200 and enables the garment 200 to communicate via one or more wireless communication protocols such as used for communication over: a wireless wide area network (WWAN), a wireless metroarea network (WMAN), a wireless local area network (WLAN), a wireless personal area network (WPAN), Bluetooth® Low Energy, Bluetooth® Mesh, Bluetooth® 5, Thread, Zigbee, IEEE 802.15.4, Ant, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communicators may be provided for communicating over a combination of different communication protocols.

The electronics module 100 may comprise a Universal Integrated Circuit Card (UICC) that enables the electronics module 100 to access services provided by a mobile network operator (MNO) or virtual mobile network operator (VMNO). The UICC may include at least a read-only memory (ROM) configured to store an MNO/VMNO profile that the wearable article can utilize to register and interact with an MNO/VMNO. The UICC may be in the form of a Subscriber Identity Module (SIM) card. The electronics module 100 may have a receiving section arranged to receive the SIM card. In other examples, the UICC is embedded directly into a controller of the electronics module 100. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to electronics modules 100. The electronics modules 100 may comprise a secure element that represents an embedded Universal Integrated Circuit Card (eUICC).

The interface 111 is arranged to communicatively couple with a sensing component of the garment 200 (FIG. 1) so as to receive a signal from the sensing component. The processor 109 is communicatively coupled to the interface 111 and is arranged to receive the signals from the interface 111. The interface 111 may form a conductive coupling or a wireless (e.g. inductive) communication coupling with the electronics components of the garment 200. The interface 111 may comprise electrical contacts 121, 123 such as those shown in FIGS. 2-7, 9, 11, 14, 17-19, and 22-26 for example.

The electronics module 100 is mounted on a garment 200 (FIG. 1) and conductively connected to sensing components such as electrodes of the garment via electrically conductive pathways of the garment 200. In a particular example, the sensing components are electrodes used to measure electro potential signals such as electrocardiogram (ECG) signals.

The processor 109 may be a component of a controller such as a microcontroller. The controller may have an integral communicator such as a Bluetooth® antenna. The controller may have an internal memory and may also be communicatively connected to an external memory of the electronics module such as a NAND Flash memory. The memory is used to for the storage of data when no wireless connection is available between the electronics module 100 a mobile device 300 (FIG. 1). The processor 109 is connected to the interface 111, 121, 123 via an analog-to-digital converter (ADC) fronted end and an electrostatic discharge (ESD) protection circuit. The ADC fronted end converts the raw analog signal received from sensing components of the garment 200 into a digital signal. The ADC frontend may also perform filtering operations on the received signals.

Figure 9:
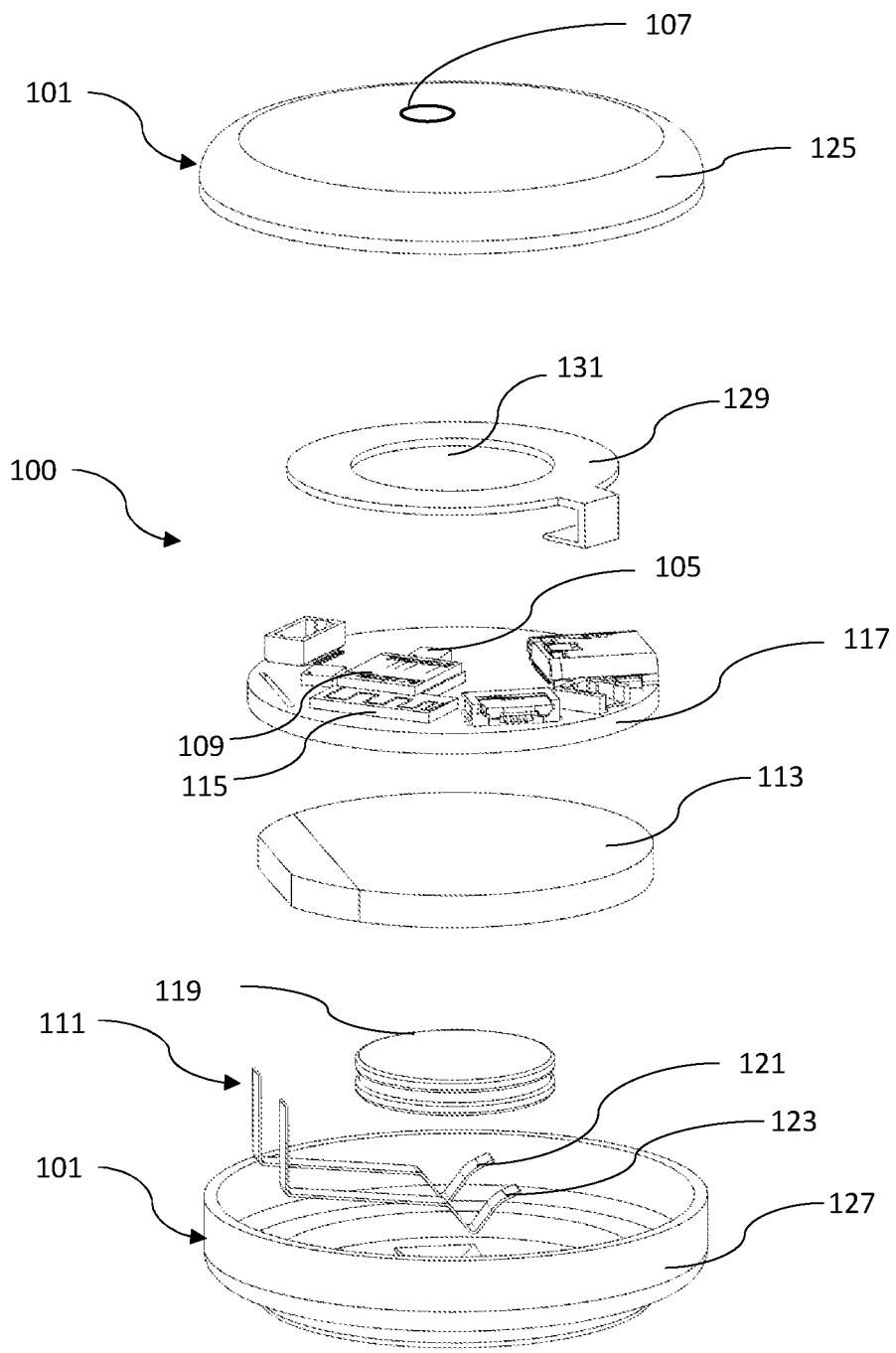
FIG. 9 shows an exploded view of yet another example electronics module according to aspects of the present disclosure.

Referring to FIG. 9, there is shown an exploded view of an example electronics module 100 according to aspects of the present disclosure.

The electronics module 100 comprises a processor 109, electronics component 105, and first communicator 115 provided on a printed circuit board 117. The power source 113 is provided separately and below the printed circuit board 117. A second communicator 129 in the form of an NFC antenna 129 is also provided. The NFC antenna 129 is positioned above the printed circuit board 117 and comprises an aperture 131 such that the NFC antenna 129 does not obscure the electronics component 105. The electronics module 100 further comprises the interface 111. The interface 111 comprises a magnet 119, and two conductive prongs 121, 123.

The components of the electronics module 100 are provided within a housing 101 formed of a top enclosure 125 and a bottom enclosure 127. In this example, the outer layer of flexible material is not provided but may be included if desired according to aspects of the present disclosure. The housing 101 comprises an opening 107 which is aligned with the electronics component 105 such that the electronics component has line of sight through the opening 107 Of course, a top enclosure 125 and bottom enclosure 127 are not required in all aspects of the present disclosure.

The NFC antenna 129 is provided proximate to the top enclosure 125. The bottom enclosure 127 is closest to the body of the wearer in use and the top enclosure 125 is furthest away from the body of the wearer in use. Beneficially, providing the NFC antenna 129 proximate to the top enclosure 125 minimises the communication distance between the NFC antenna 129 and the mobile device 300.

Figure 10:
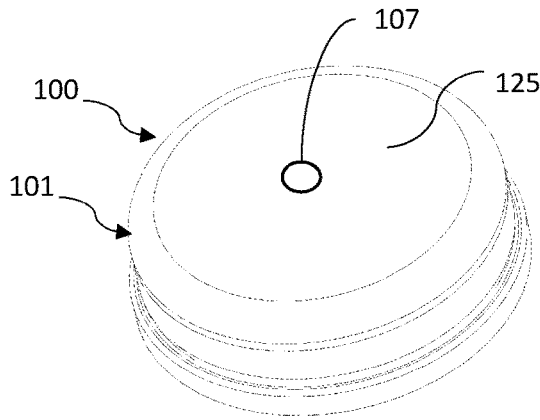
FIGS. 10 and 11 show perspective views of the electronics module of FIG. 9.
Figure 11:
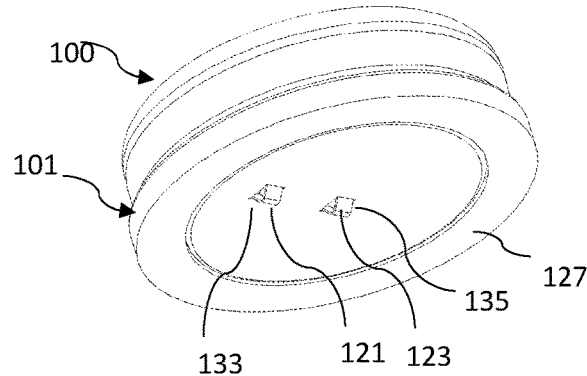

Referring to FIGS. 10 and 11, there is shown an electronics module 100 according to aspects of the present disclosure. The electronics module 100 may be the same as any of the electronics modules 100 as described above in relation to FIGS. 1 to 9. The electronics module 100 comprises a housing 101 which contains the components of the electronics module 100. In this example, the outer layer of flexible material is not provided but may be included if desired according to aspects of the present disclosure.

The housing 101 comprises a top enclosure 125 and a bottom enclosure 127. The bottom enclosure 127 is closest to the body of the wearer in use and the top enclosure 125 is furthest away from the body of the wearer in use. First and second conductive prongs 121, 123 extend from openings 133, 135 in the bottom enclosure 127. The first and second conductive prongs 121, 123 are able to electrically conductively connect with conductive elements provided on a textile so as to electrically conductively connect the electronics module 100 to the conductive elements of the textile. The use of conductive prongs 121, 123 to electrically conductively connect the electronics module 100 to the textile are not required in all aspects of the present disclosure. Other forms of conductive connection may be provided such as via conductive studs or pins. In addition, a conductive connection may not be required as a wireless communication connection may be formed between the electronics module 100 and electronics components of the textile to allow for data exchange between the electronics module 100 and the electronics components of the textile. In one example, the electronics module 100 comprises an NFC coil proximate to the bottom enclosure 127 and the textile material comprises a corresponding NFC coil These NFC coils form a communicative coupling when the electronics module 100 is brought into proximity with the textile to allow for data exchange.

Figure 12:
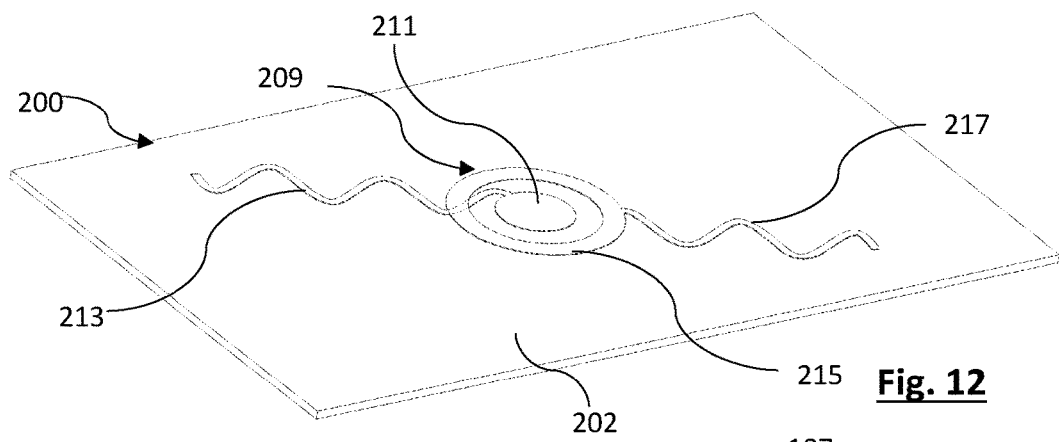
FIG. 12 shows a perspective view of an example component of a garment according to aspects of the present disclosure.

Referring to FIG. 12, there is shown an example textile layer of a garment 200 according to aspects of the present disclosure. The garment 200 comprises a textile material 202 and conductive elements 211, 213, 215, 217 provided on the textile material 202. The conductive elements 211, 213, 215, 217 comprise the terminal region 209 of FIGS. 7 and 10. The terminal region 209 comprises a first terminal 211. A first electrically conductive pathway 213 extends from the first terminal 211 to a first electrode (not shown). The first electrically conductive pathway 213 therefore electrically connects the first terminal 211 to the first electrode. The conductive elements 211, 213, 215, 217 further comprise a second terminal 215 and a second electrically conductive pathway 217 that extends from the second terminal 215 to a second electrode (not shown). The second electrically conductive pathway 217 therefore electrically connects the second terminal 215 to the second electrode. The first and second terminals 211, 215 are arranged as concentric circles. A portion of the first electrically conductive pathway 213 extends under the second terminal 215. An insulating layer (not shown) insulates the first electrically conductive pathway 213 from the second terminal 215.

This is just one example arrangement of conductive elements on a textile. Different types of conductive elements may be used for the electrically conductive pathways and the terminals which join the electronics module to the electrically conductive pathways.

For example, the electrically conductive pathways may be formed from a conductive thread or wire. The conductive thread or wire may be woven or otherwise incorporated into a tape or fabric panel. The electrically conductive pathway may be an electrically conductive track or film. The electrically conductive pathway may be a conductive transfer. The conductive material may be formed from a fibre or yarn of the textile. This may mean that an electrically conductive materials are incorporated into the fibre/yarn. The conductive material may be a conductive rubber.

For example, the terminals may be formed from conductive thread or wire. The conductive thread or wire may be woven or otherwise incorporated into a tape or fabric panel. The terminals may be formed from electrically conductive track or film. The terminals may be a conductive transfer. The conductive material may be formed from a fibre or yarn of the textile. This may mean that an electrically conductive materials are incorporated into the fibre/yarn. The terminals may be formed from a conductive rubber. The terminals may be formed from a printed circuit board and, in particular, a flexible printed circuit board.

In some examples, the conductive pathways may be provided on the underside surface of the textile. In some examples, an aperture may be provided in the textile so as to allow the electronics module to conductively connect to the conductive pathways.

Figure 13:
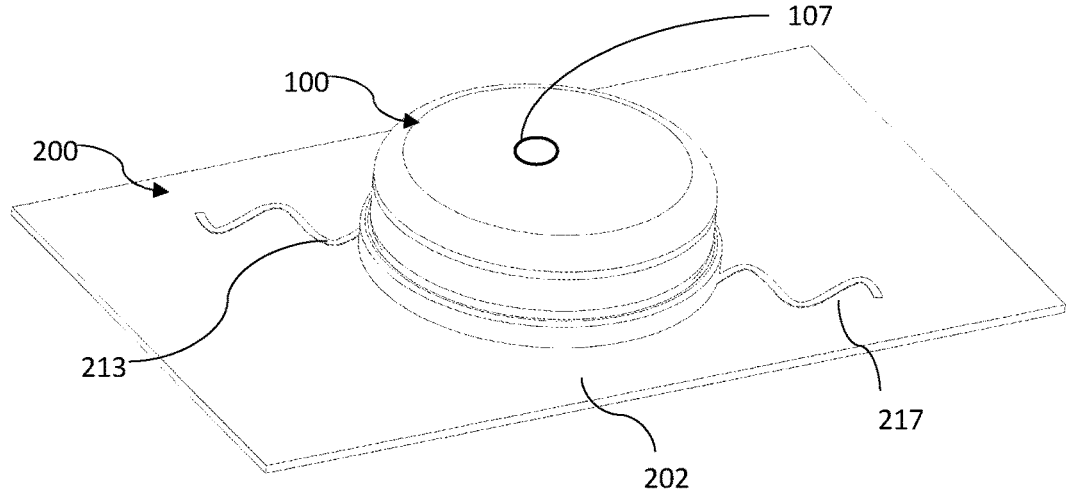
FIG. 13 shows a perspective view of the electronics module of FIGS. 10 and 11 mounted on the garment of FIG. 12.

Referring to FIG. 13, there is shown the electronics module 100 of FIGS. 10 and 11 attached to the garment 200 of FIG. 12. The first conductive prong 121 is brought into conductive electrical contact with the first terminal 211 and the second conductive prong 123 is brought into conductive electrical contact with the second terminal 215. A magnet (FIG. 9, element 119) may be provided in the electronics module 100 and on the underside of the garment 200 so as to maintain the electronics module 100 in releasable attachment with the garment 200.

Figure 14:
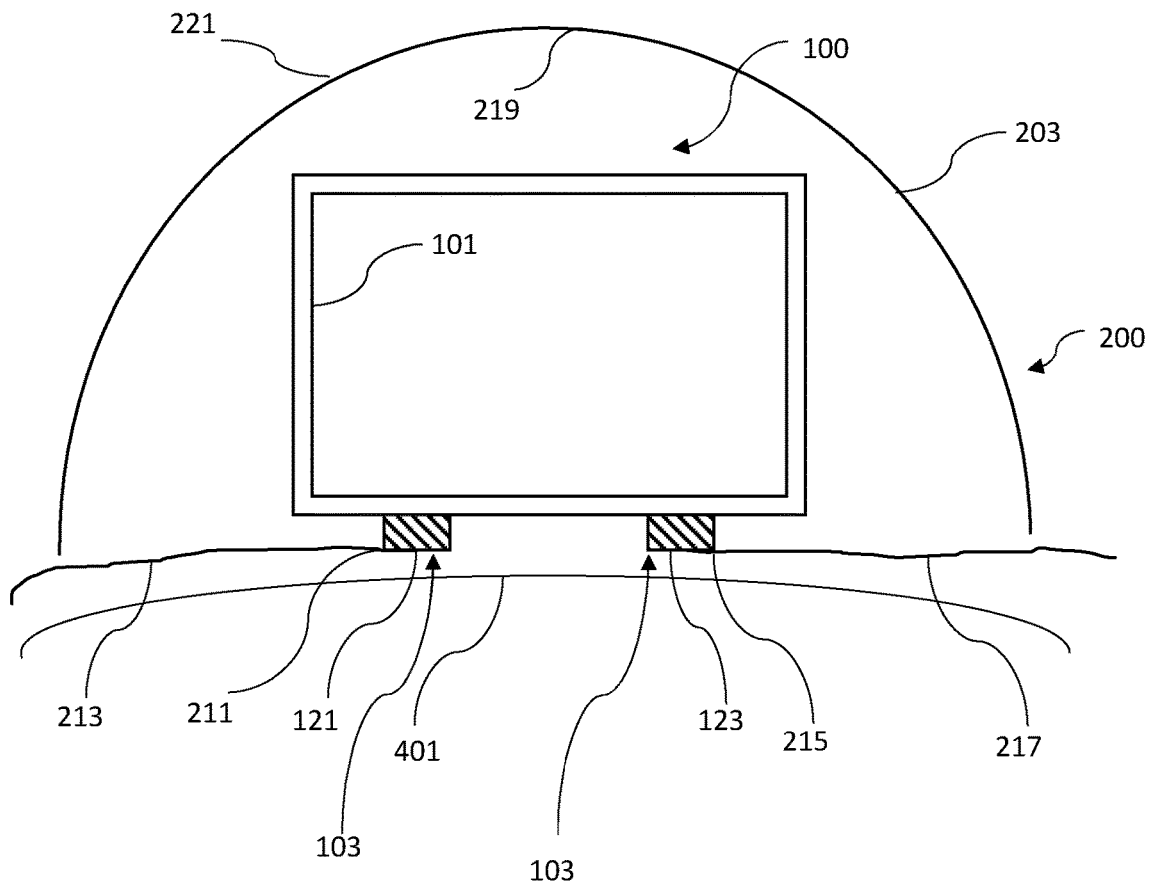
FIG. 14 shows a sectional view of yet another example apparatus according to aspects of the present disclosure.

Referring to FIG. 14, there is shown a sectional view of an apparatus comprising a garment 200 and an electronics module 100 disposed within an electronics module holder 203 of the garment 200. The garment 200 is being worn by a user and is proximate to the skin surface 401 of the user. The electronics module holder 203 in this example is an elasticated pocket 203 positioned on the outside surface of the garment 200 and may be the same as the pocket 203 described above in reference to FIG. 2.

The electronics module 100 comprises a rigid housing 101. One or more electrical components are provided within the rigid housing 101. An outer layer of flexible material 103 covers at least part of the rigid housing 101. The outer layer of flexible material 103 comprises two sections 121, 123 of flexible material 103 that are spaced apart from one another on the bottom surface of the rigid housing 101. The two sections 121, 123 of the flexible material 103 comprise flexible conductors 121, 123 that act as electrical contacts 121, 123 for the electronics module 100. The flexible conductors 121, 123 therefore provide the interface by which the electronics module 100 is conductively connected to the garment 200.

The first electrical contact 121 conductively connects with a first terminal region 211 of the garment 200. The first terminal region 211 enables the electronics module 100 to conductively connect to sensing components of the garment 200 via first electrically conductive pathway 213 of the garment 200. The sensing components may be one or more electrodes. The second electrical contact 123 conductively connects with a second terminal region 215 of the garment 200. The second terminal region 215 enables the electronics module 100 to conductively connect to sensing components of the garment 200 via second electrically conductive pathway 217 of the garment 200. The sensing components may be one or more electrodes.

The use of flexible conductors 121, 123 as the electrical contacts means that hard pieces of conductive metallic material such as poppers or studs are not required to electrically connect the electronics module 100 to the garment 200. This not only improves the look and feel of the garment 200 but also reduces manufacturing costs as it means that hardware features such as additional eyelets and studs do not need to be incorporated into the garment 200 to provide the required connectivity. In addition, the use of a outer layer of flexible material 103 covering at least part of the rigid housing 101 simplifies the construction of the electronics module 100 at least because rigid metallic conductors do not need to be incorporated into the electronics module 100. An additional problem with rigid metallic conductors is that their hard, abrasive, surfaces may rub against conductive elements such as conductive thread of the garment and cause the conductive thread to fray.

Figure 15:
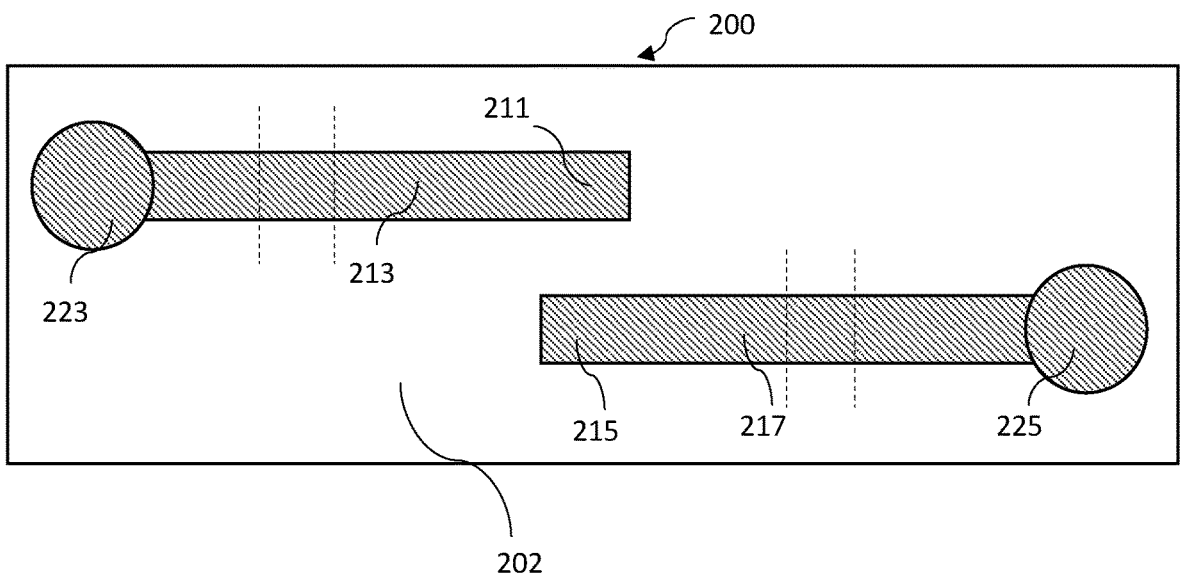
FIGS. 15 and 16 show a schematic diagram of an example wearable article according to aspects of the present disclosure before and after the attachment of an electronics module.
Figure 16:
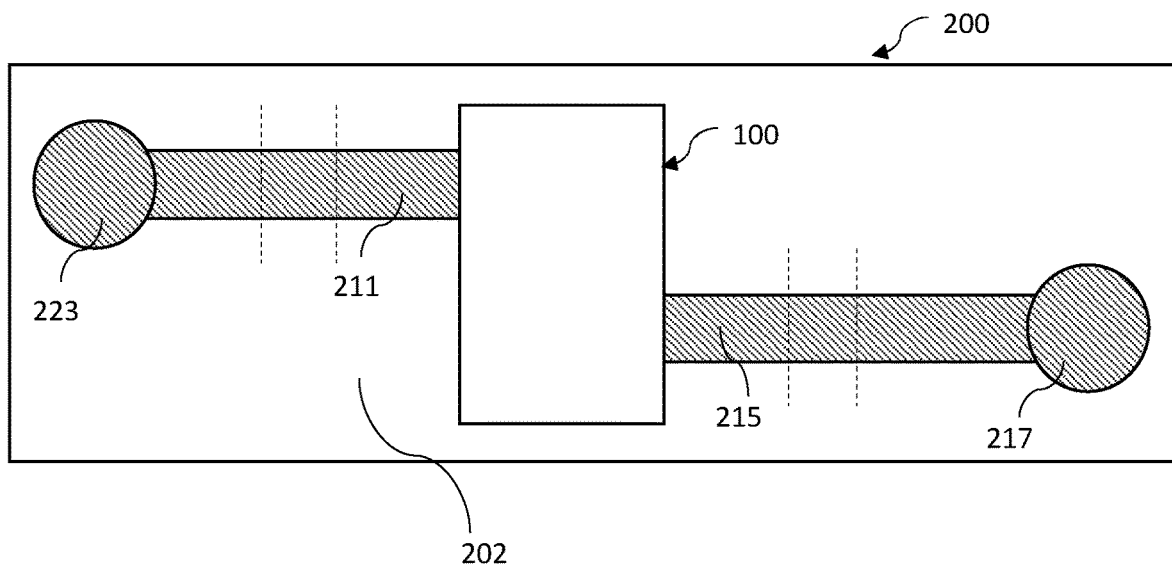

Referring to FIGS. 15 and 16, there is shown a simplified schematic view of a textile material 202 of the garment 200 and an electronics module 100 positioned on the textile material 202. The textile material 202 comprises conductive elements 211, 213, 215, 217, 223, 225. The textile material 202 comprises a first terminal region 211 which contacts with the first electrical contact 121 of the electronics module 100 in use. The first terminal region 211 is electrically connected to a first electrode 223 via electrically conductive pathway 213. The textile material 202 comprises a second terminal region 215 which contacts with the second electrical contact 123 of the electronics module 100 in use. The second terminal region 215 is electrically connected to a second electrode 225 via electrically conductive pathway 217.

Figure 17:
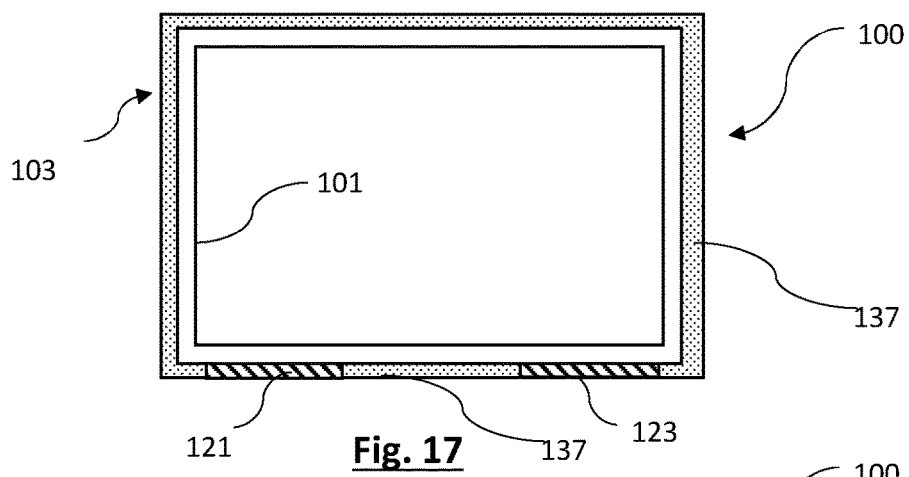
FIG. 17 shows a schematic diagram of yet another example electronics module according to aspects of the present disclosure.

Referring to FIG. 17, there is shown a schematic view of another example electronics module 100 according to aspects of the present disclosure. The electronics module 100 comprises a rigid housing 101 and an outer layer of flexible material 103 that covers the top and bottom of the rigid housing 101. The outer layer of flexible material 103 comprises first flexible conductor 121 and second flexible conductor 123 covering the bottom of the rigid housing. The first and second flexible conductors 121, 123 are separated from one another by the remaining sections 137 of the outer layer of flexible material 103. The remaining sections 137 of the outer layer of flexible material 103 are not conductive and are made of a fabric material. The first and second flexible conductors 121, 123 are made of a conductive fabric material which may comprise conductive strands which are woven or otherwise incorporated into the fabric or conductive fibres or yarns which have a conductive coating. Conductive elements used in the flexible conductors 121, 123 include, but are not limited to, an electrically conductive carbon-based material such as graphene, a conductive polymer such as PEDOT or a conductive metal such as nickel, copper, gold, silver or titanium.

Figure 18:
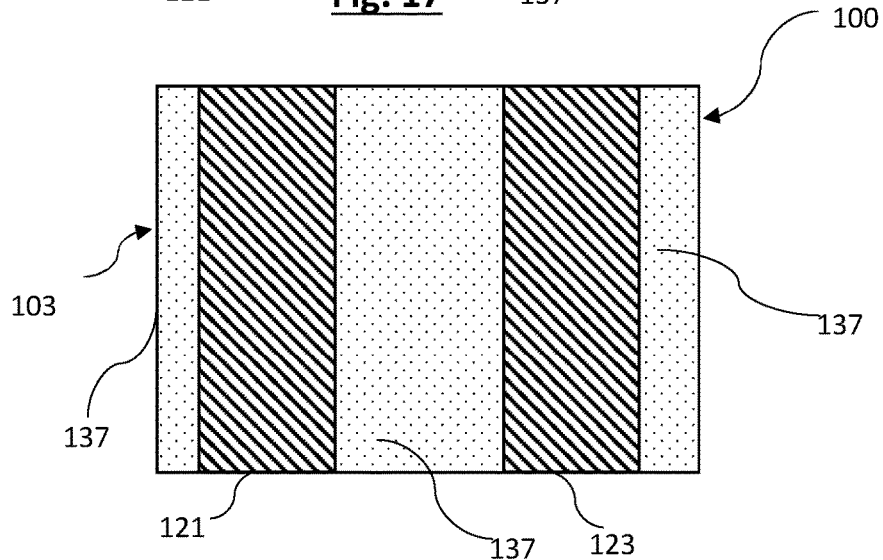
FIG. 18 shows the bottom surface of the electronics module in FIG. 17.

Referring to FIG. 18, there is shown a view of the bottom surface of the electronics module 100. The first and second flexible conductors 121, 123 extend along the length of the bottom surface and are generally parallel to one another. The remaining sections 137 may incorporate branding or decorative elements.

Figure 19:
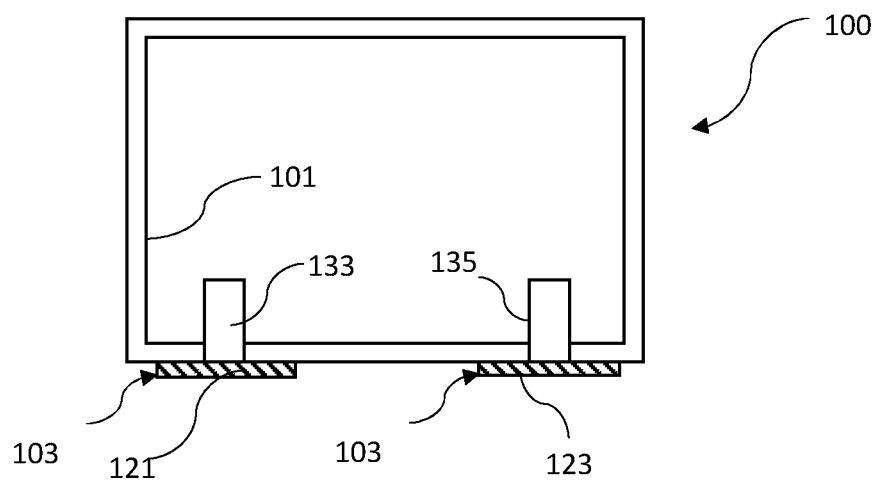
FIG. 19 shows a schematic diagram of yet another example electronics module according to aspects of the present disclosure.

Referring to FIG. 19, there is shown a schematic view of another example electronics module 100 according to aspects of the present disclosure. The electronics module 100 comprises a rigid housing 101 and an outer layer of flexible material 103 in the form of first and second flexible conductors 121, 123 that are spaced apart from one another. In this example, conductive elements 133, 135 extend through openings in the rigid housing 101 to electrically connect the flexible conductors 121, 123 to electronic components of the electronics module 100 disposed within the rigid housing 101. The conductive elements 133, 135 may be force-biased conductors 133, 135 such as spring-loaded pins 133, 135.

Referring to FIGS. 20 to 23 there is shown another example electronics module 100 according to aspects of the present disclosure. The electronics module 100 in this example has a generally circular cross-section. The present disclosure is not limited to any particular shape of electronics module 100. The electronics module 100 may have a square cross-section, rectangular cross-section, oblong cross-section or any other shaped cross-section.

Figure 20:
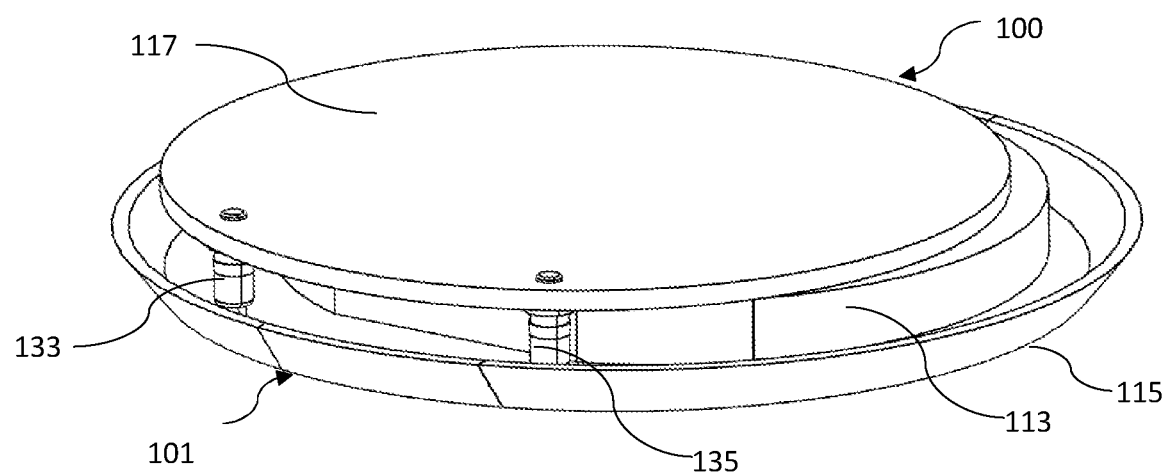
FIGS. 20 to 23 show sectional views of yet another example electronics module according to aspects of the present disclosure.
Figure 21:
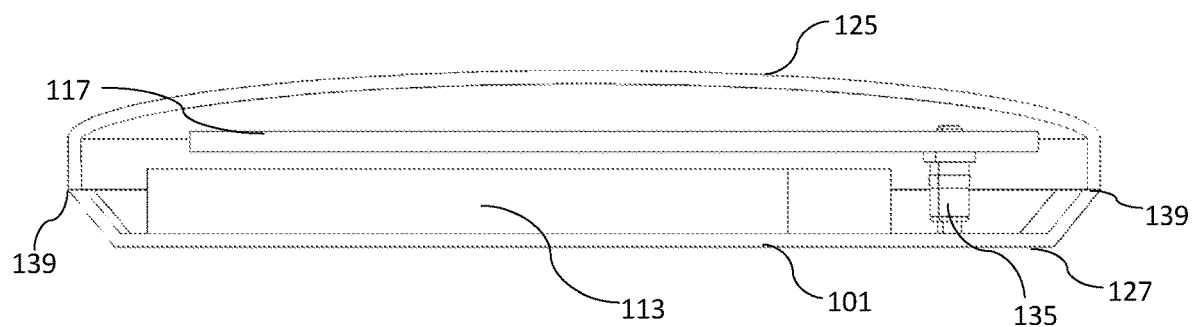

FIGS. 20 and 21 show the electronics module 100 without the outer layer of flexible material 103. FIG. 20 shows the electronics module 100 without the top enclosure 125 of the rigid housing 101 while the top enclosure 125 is included in FIG. 21. The electronics module 100 comprises a printed circuit board 117 and power source 113 disposed within the rigid housing 101. The printed circuit board 117 and power source 113 may be the same as the printed circuit board of FIG. 9. The electronics module 100 may comprise other components similar to those described above in relation to FIG. 9.

Conductors 133, 135 extend from the printed circuit board 117 so as to electrically connect the printed circuit board 117 to the flexible conductors. The conductors 133, 135 in this example are spring-loaded pins 133, 135 which are also known as pogo-pins 133, 135.

FIGS. 20 and 21 show that the top and bottom enclosures 125 and 127 are snap fitted together. A sealant material such as bead of silicon may be applied to the lip of one or both of the top and bottom enclosures 125, 127 prior to joining them together so as to form a water-tight seal at the join 139 between the top and bottom enclosure 127. This may beneficially protect against water ingress into the electronics module 100. Therefore, the electronics module 100 is waterproof while still enabling electrical connection between internal components of the electronics module and external components.

Figure 22:
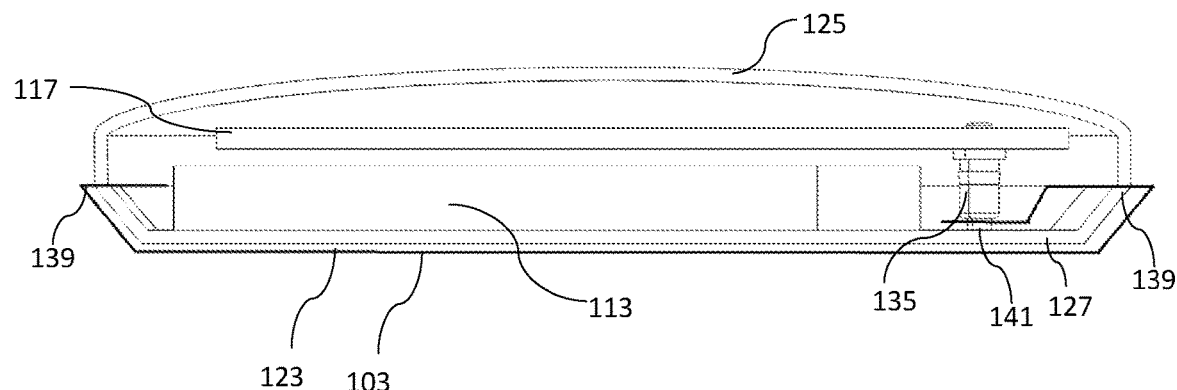
Figure 23:
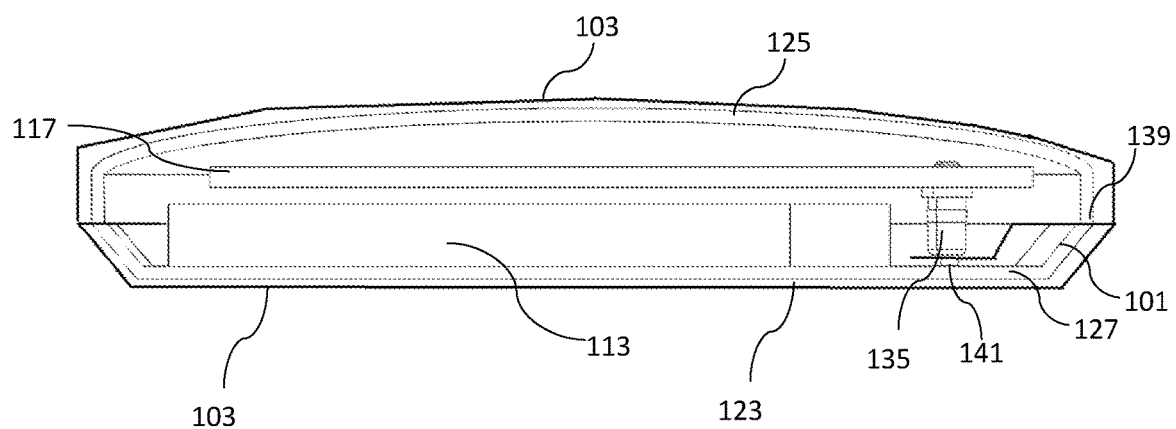

FIGS. 22 and 23 show the electronics module 100 with the outer layer of flexible material 103. FIG. 22 shows the shows the electronics module 100 without the top enclosure 125 of the rigid housing 101 while the top enclosure 125 is included in FIG. 23. The outer layer of flexible material 103 extends into the housing 101 and is thus clamped in place at the join between the top and bottom enclosure 137. The second flexible conductor 123 extends down the inside of the bottom enclosure 127 to allow for the pogo pin 135 to contact and press against the second flexible conductor 123 at contact point 141. This enables the pogo pin 135 to be conductively connected to the second flexible conductor 123. A similar arrangement is provided for the first flexible conductor 121 which is not shown in these Figures. The snap-fit between the top and bottom enclosures 125, 127 helps ensure that the pogo pin 135 is under and constant and even pressure, and is thus in constant contact with the second flexible conductor 123. The top enclosure 125 may comprise mounting pins to help apply pressure to the printed circuit board 117 and thus to the pogo pins 131, 135.

In a preferred example, the pogo pins 131, 135 are suitable to be applied using a surface mount technology which lowers manufacturing costs. An example of such as pogo pin is the P70-2000045R pogo pin from Harwin PLC. Such surface mount suitable pogo pins may include additional locating pins for use in the surface mount process. These locating pins may, beneficially, provide additional structural support and reduce translational movement of the pogo pins relative to the printed circuit board.

The present disclosure is not limited to pogo pins. Other forms of conductor and particularly force-biased conductors may be used to connect the printed circuit board 117 to the flexible conductors 121, 123. For example, conductive leaf springs may be used.

Moreover, other processes could be used to connect the printed circuit board 117 to the flexible conductors 121, 123 such as by soldering the connections, terminating the printed circuit board 117 by means of a fixing such as a screw or bolt, or by crimping the flexible conductors 121, 123 to the printed circuit board 117, These approaches are generally less preferred as they are more costly and labour intensive than the implementations described above, but are still within the scope of the present disclosure.

Figure 24:
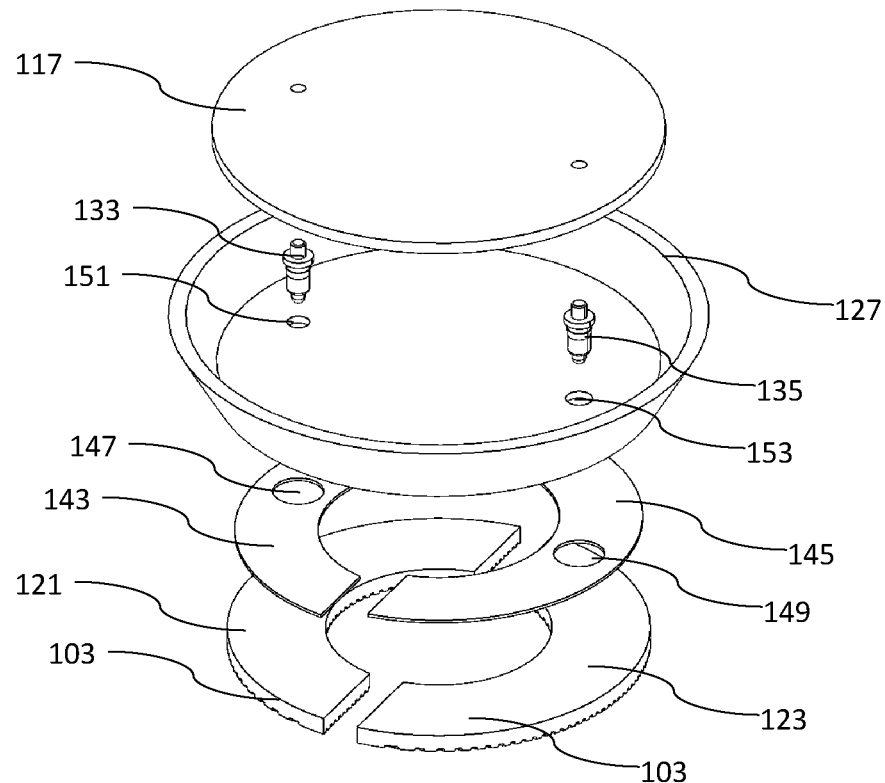
FIG. 24 shows an exploded view of an example electronics module according to aspects of the present disclosure.
Figure 25:
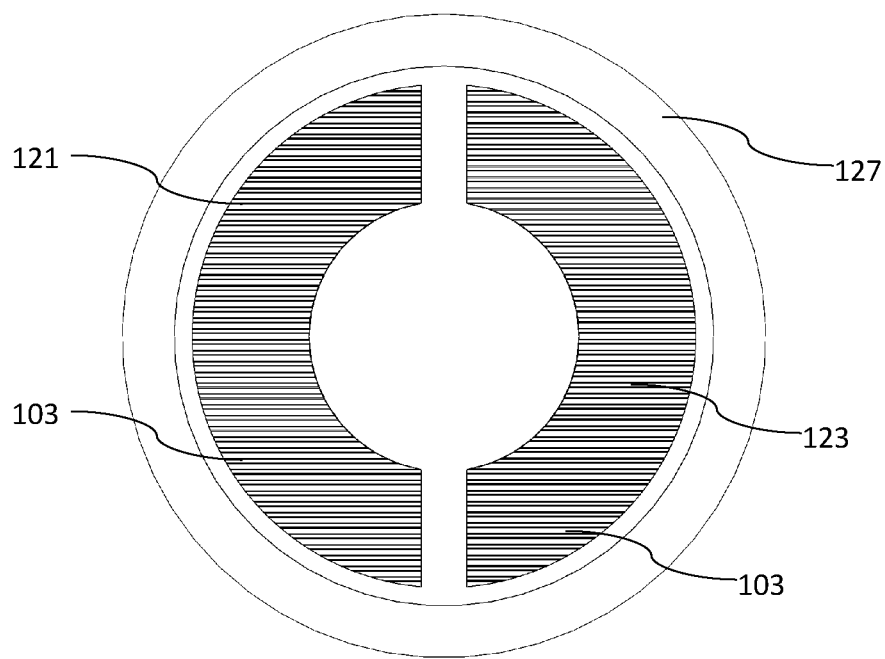
FIG. 25 shows a view of the bottom surface of the electronics module of FIG. 24.
Figure 26:
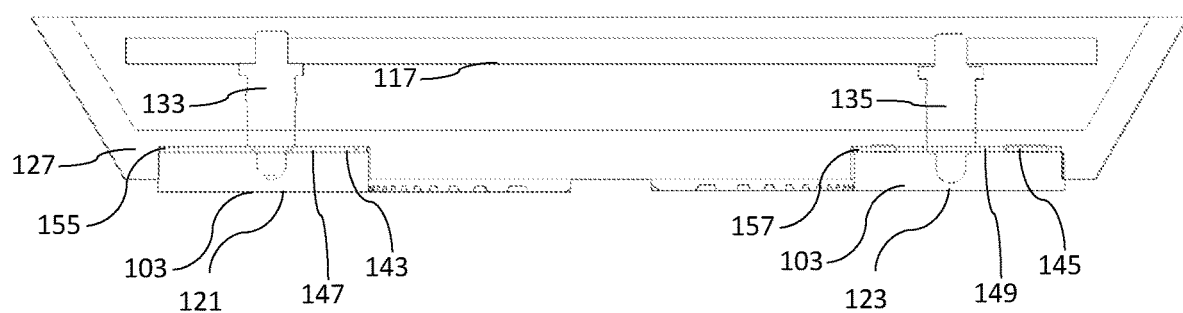
FIG. 26 shows a sectional view of the electronics module of FIG. 24.

Referring to FIGS. 24 to 26, there is shown another example electronics module 100 according to aspects of the present disclosure. In these Figures, the top enclosure 125 is omitted so that the internal components of the electronics module are visible.

The outer layer of flexible material 103 comprises two separate pieces of conductive elastomeric material 121, 123 that form the first and second flexible conductors 121, 123. The conductive elastomeric material used in this example is a conductive silicone rubber material, but other forms of conductive elastomeric material may be used. Beneficially, elastomeric material such as conductive silicone rubber can have an attractive visual appearance and may easily be moulded or extruded to have branded or other visual elements.

The elastomeric material is made conductive by distributing a conductive material into the elastomeric material. Conductive particles such as carbon black and silica are commonly used to form conductive elastomeric materials but the present disclosure is not limited to these examples. The contact pads 121, 123 may also comprise a 2D electrically conductive material such as graphene or a mixture or composite of an elastomeric material and a 2D electrically conductive material.

The conductive elastomeric material 121, 123 may be textured to provide additional grip when positioned on the garment 200. The texture may be, for example, a ribbed or knurled texture. The elastomeric material 121, 123 shown in the Figures has a ribbed texture.

The first and second flexible conductors 121, 123 together for a split-ring shape, but other shapes and arrangements of the flexible conductors 121, 123 are within the scope of the present disclosure.

The outer surface of the bottom enclosure 127 has recesses 155, 157 sized to receive the flexible conductors 121, 123. The recesses 155, 157 have a push tight to ensure that no dust or debris is able to enter the electronics module 100.

Double sided-adhesive layers 143, 149 are used to adhere the flexible conductors 121, 123 to the outer surface of the bottom enclosure 127. The adhesive layers 143, 149 may be adhesive transfer tape 143, 147 such as adhesive transfer tape 467 and adhesive transfer tape 468 provided by 3M.

The pogo pins 133, 135 extend through openings 151, 153 in the bottom enclosure 127 and openings 147, 149 in the adhesive layers 143, 145 so as to electrically connect to the first and second flexible conductors 121, 123. The openings 147, 149 in the adhesive layers 143, 135 are larger than the openings in the bottom enclosure 127 to help ensure that adhesive does not interfere with the pogo pin mechanism or cause a potential short circuit.

The snap fit between the top enclosure 125 and the bottom enclosure 127 applies pressure to the printed circuit board 117 and thus helps ensure that the pogo pins 133, 135 are in constant contact with the flexible conductors 121, 123.

Beneficially, in this arrangement, the elastomeric flexible conductors 121, 123 seal the openings 151, 153 in the bottom enclosure 127 and thus prevent water ingress into the electronics module 100. Therefore, the electronics module 100 is waterproof while still enabling electrical connection between internal components of the electronics module and external components.

While this example shows pogo pins 133, 135 the present disclosure is not limited to pogo pins 133, 135 and other forms of conductors such as spring pins may be used. A power source is not shown in FIGS. 24 to 26 but may be provided under the printed circuit board 117.

In the examples of FIGS. 20-26, force-biased conductors 133, 135 extend from the electronics component 117 (printed circuit board 117) to conductive connect the electronics component 117 to the conductive material 121, 123. The connection between the force-biased conductors 113, 135 and the conductive material 121, 123 may be within the housing (FIGS. 20-23) or external to the housing (FIGS. 24 to 26). Pressure applied to the force-biased conductors 133, 135 urges them against the conductive material 121, 123 to form the conductive electrical connection. This approach means that the force-biased conductors 133, 135 do not need to be welded or otherwise attached to the conductive material 121, 123. This simplifies the manufacturing process.

The electronics modules 100 of the present disclosure are able to be manufactured in a simple and cost effective process. Generally, separate components of the electronics module 100 are able to be manufactured separately and then assembled together. The manufacturing techniques do not require overmoulding technique which are complicated, expensive and prone to failure. Typically, overmoulding requires the electronics components to be coated in a protective coating prior to overmoulding, and also require the use of expensive jigs to hold components in place during the moulding operation. Generally, overmoulding techniques are labour intensive and thus expensive.

Referring to the example of FIGS. 20 to 23, the printed circuit board 117 and pogo pins 113, 135 may be assembled together. Separately, the housing 125, 127 may be manufactured using techniques such as injection moulding. Separately still, the conductive material 121, 123 may be manufactured.

The conductive material 121, 123 may be provided to cover at least part of the external surface of the bottom enclosure 127. Edges of the conductive material 121, 123 may be folded into the bottom enclosure 127. The printed circuit board 117 and pogo pins 133, 135 may be provided in the bottom enclosure 127 such that the pogo pins 133, 135 contact the conductive material 121, 123. The top enclosure 125 is attached to the bottom enclosure 127 such as by using a snap-fit mechanism. The top enclosure 125 may apply pressure to the printed circuit board 117 so as to help urge the pogo pins 133, 135 into electrical contact with the conductive material 121, 123.

Referring to the example of FIGS. 24 to 26, the printed circuit board 117 and pogo pins 133, 135 may be assembled together. Separately, the housing 125, 127 may be manufactured using techniques such as injection moulding. Separately still, the conductive material 121, 123 may be manufactured.

To manufacture the electronics module 100, the conductive material 121, 123 is attached to the external surface of the bottom enclosure 127. The printed circuit board 117 and pogo pins 133, 135 are provided in the bottom enclosure 127 such that the pogo pins 133, 135 extend through the opening 151, 153 and contact the conductive material 121, 123. The top enclosure 125 is attached to the bottom enclosure 127 such as by using a snap-fit mechanism. The top enclosure 125 may apply pressure to the printed circuit board 117 so as to help urge the pogo pins 133, 135 into electrical contact with the conductive material 121, 123.

While the examples of FIGS. 14 to 26 show electronics modules 100 with two flexible conductors 121, 123 it will be appreciated that the present disclosure is not limited to any particular number of flexible conductors. One flexible conductor may be provided. Two or more flexible conductors may be provided. The number of flexible conductors will depend on the number of terminals in the garment to be connected to. For example, there may be 4, 6 or 10 flexible conductors. It will be appreciated that additional flexible conductors may be electrically connected to the printed circuit board through the use of additional pogo pins 133, 135 or other conductors.

The electronics modules 100 shown in the examples of FIGS. 14 to 26 may comprise any or all of the features of the electronics module 100 of FIGS. 1 to 13.

In the present disclosure, the electronics module may also be referred to as an electronics device or unit. These terms may be used interchangeably.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA), programmable System on Chip (pSoC), or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

EMBODIMENTS

Embodiment 1. A wearable assembly comprising:
a wearable article comprising a sensing component;
an electronics module arranged to be removably coupled to the wearable article, the electronics module comprising:
a housing;
a processor disposed within the housing;
an interface element arranged to interface with the sensing component of the wearable article so as to receive signals from the sensing component and provide the same to the processor; and
a sensor disposed within the housing, the sensor being arranged to monitor a property of the environment external to the electronics module through the housing;
wherein the housing is constructed such that the sensor has line of sight through the housing.

Embodiment 2. A wearable assembly as set forth in Embodiment 1, wherein the interface element comprises a conductive material, and wherein the conductive material provides a surface arranged to interface with a conductive region of the wearable article so as to conductively connect the electronics module to the conductive region of the wearable article.

Embodiment 3. A wearable assembly as set forth in Embodiment 2, wherein the interface element comprises a first conductive material and a second conductive material, wherein the first and second conductive materials are spaced apart from one another.

Embodiment 4. A wearable assembly as set forth in Embodiment 3, wherein the sensor is located between the first and second conductive materials.

Embodiment 5. A wearable assembly as set forth in any one of Embodiments 2 to 4, wherein the conductive material forms a contact pad.

Embodiment 6. A wearable assembly as set forth in any one of Embodiments 2 to 5, wherein the conductive material is formed of a flexible conductive material.

Embodiment 7. A wearable assembly as set forth in Embodiment 6, wherein the flexible conductive material is a conductive elastomeric material.

Embodiment 8. A wearable assembly as set forth in any preceding Embodiment, wherein the housing comprises an opening aligned with the sensor such that the sensor has line of sight through the housing.

Embodiment 9. A wearable assembly as set forth in any one of Embodiments 1 to 7, wherein the housing comprises a window aligned with the sensor such that the sensor has line of sight through the window, optionally wherein the window is constructed from a transparent, translucent, or light-diffracting material.

Embodiment 10. A wearable assembly as set forth in any preceding Embodiment, wherein the sensor comprises one or more of an altitude sensor, optical sensor, pressure sensor, temperature sensor, humidity sensor, presence sensor, and air quality sensor.

Embodiment 11. A wearable assembly as set forth in Embodiment 10, wherein the sensor comprises an infrared temperature sensor arranged to measure the skin surface temperature of a user wearing the wearable article.

Embodiment 12. A wearable assembly as set forth in Embodiment 10, wherein the optical sensor comprises a pulse oximeter.

Embodiment 13. A wearable assembly as set forth in any preceding Embodiment, wherein the electronics module further comprises a light source disposed within the housing, the light source is arranged to emit light through the housing.

Embodiment 14. A wearable assembly as set forth in any preceding Embodiment, wherein the wearable article comprises an electronics module holder arranged to receive the electronics module.

Embodiment 15. A wearable assembly as set forth in Embodiment 14, wherein the electronics module holder comprises a pocket.

Embodiment 16. A wearable assembly as set forth in Embodiment 15, wherein the pocket is arranged to apply a compressive force to hold the electronics module in position within the pocket so as to communicatively couple the interface element to the sensing component of the wearable article.

What is claimed is:
1. A wearable article comprising:
an electronics module comprising:
a housing comprising a top surface and a bottom surface, wherein the bottom surface is arranged to be closer to the skin of a user than the top surface in use;
an optical sensor disposed within the housing proximate to the bottom surface of the housing, the optical sensor being arranged to monitor a property of an environment external to the electronics module through the housing, wherein the housing further comprises a window aligned with the optical sensor such that the optical sensor has line of sight through the window;
a processor disposed in the housing;
a communicator disposed in the housing and comprising a near-field communication (NFC) antenna, wherein the NFC antenna comprises an aperture and the aperture is aligned with the window;
a printed circuit board on which the processor is provided, and wherein the NFC antenna is positioned above the printed circuit board and processor, and the NFC antenna is positioned proximate to the top surface of the housing; and
a compression garment comprising an electronics module holder in the form of a pocket arranged to removably receive the electronics module, the compression garment comprises an opening arranged such that when the electronics module is provided in the pocket, the optical sensor is aligned with the opening in the compression garment and has line of sight with a skin surface of a wearer of the compression garment, and wherein the pocket comprises an inner surface facing the electronics module when positioned in the pocket and an outer surface forming part of the outer surface of the compression garment, wherein the inner surface of the pocket comprises a gripping material which increases friction between the pocket and the electronics module when positioned in the pocket.

2. A wearable article as claimed in claim 1, wherein the pocket comprises the opening.

3. A wearable article as claimed in claim 1, wherein the pocket is positioned on an outside surface of the compression garment.

4. A wearable article as claimed in claim 1, wherein the pocket is positioned on an inner surface of the compression garment.

5. A wearable article as claimed in claim 1, wherein the pocket is an elasticated pocket arranged to apply a compressive force to help hold the electronics module in a generally fixed position within the pocket.

6. A wearable article as claimed in claim 1, wherein the gripping material comprises a silicone-based coating.

7. A wearable article as claimed in claim 1, wherein the inner surface of the pocket comprises a number of lines or dots of gripping material.

8. A wearable article as claimed in claim 1, wherein the electronics module further comprises a light source disposed within the housing, the light source is arranged to emit light through the housing.

9. A wearable article as claimed in claim 1, wherein the electronics module further comprises an interface element coupled with a sensing component of the wearable article, wherein said interface element receives signals from the sensing component, and wherein the interface element comprises (a) one or more electrical contacts that are in conductive communication with the sensing component, or (b) an antenna that is in a wireless communication with the sensing component.

10. A wearable article as claimed in claim 1, wherein the compression garment is an item of clothing.

11. A wearable article as claimed in claim 10, wherein the item of clothing is an item of athletic clothing.

12. A wearable article as claimed in claim 1, wherein the compression garment is a top.

13. A wearable article as claimed in claim 1, wherein the compression garment is a pair of shorts or pants.

14. A wearable article as claimed in claim 1, wherein the compression garment is an item of underwear.

15. A wearable article as claimed in claim 1, wherein the compression garment is a brassiere.

16. A wearable article as claimed in claim 1, further comprising a Bluetooth antenna.

17. A wearable article as claimed in claim 1, wherein the electronics module further comprises a rechargeable battery provided separately to the printed circuit board.

18. A wearable article as claimed in claim 17, wherein the battery is adapted to be recharged wirelessly.

19. A wearable article comprising:
  an electronics module comprising:
    a housing comprising a top surface and a bottom surface, wherein the bottom surface is arranged to be closer to the skin of a user than the top surface in use;
    an optical sensor disposed within the housing proximate to the bottom surface of the housing, the optical sensor being arranged to monitor a property of an environment external to the electronics module through the housing, wherein the housing comprises a window aligned with the optical sensor such that the optical sensor has line of sight through the window;
    a processor disposed in the housing;
    a communicator disposed in the housing and comprising a near-field communication, NFC, antenna, wherein the NFC antenna comprises an aperture and the aperture is aligned with the window;
    a printed circuit board on which the processor is provided, and wherein the NFC antenna is positioned above the printed circuit board and processor, and the NFC antenna is positioned proximate to the top surface of the housing; and
  a garment comprising an electronics module holder in the form of an elasticated pocket arranged to removably receive the electronics module and apply a compressive force to help hold the electronics module in a generally fixed position within the pocket, the garment comprises an opening arranged such that when the electronics module is provided in the pocket, the optical sensor is aligned with the opening in the garment and has line of sight with a skin surface of a wearer of the compression garment, and wherein the pocket comprises an inner surface facing the electronics module when positioned in the pocket and an outer surface forming part of the outer surface of the garment, wherein the inner surface of the pocket comprises a gripping material which increases friction between the pocket and the electronics module when positioned in the pocket.

* * * * *